(12) United States Patent
Peh et al.

(10) Patent No.: US 8,657,805 B2
(45) Date of Patent: *Feb. 25, 2014

(54) COMPLEX SHAPE STEERABLE TISSUE VISUALIZATION AND MANIPULATION CATHETER

(75) Inventors: Ruey-Feng Peh, Mountain View, CA (US); Vahid Saadat, Saratoga, CA (US); Chris A. Rothe, San Mateo, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 12/117,655

(22) Filed: May 8, 2008

(65) Prior Publication Data

US 2008/0281293 A1 Nov. 13, 2008

Related U.S. Application Data

(60) Provisional application No. 60/916,640, filed on May 8, 2007.

(51) Int. Cl.
*A61M 25/098* (2006.01)

(52) U.S. Cl.
USPC ........... 604/529; 604/523; 604/524; 604/528; 604/532; 604/95.03; 604/95.04; 604/108

(58) Field of Classification Search
USPC ........... 604/523–532, 95.01–95.05, 104–109; 606/200, 192, 194
See application file for complete search history.

(56) References Cited

U.S. PATENT DOCUMENTS

| | | |
|---|---|---|
| 623,022 A | 4/1899 | Johnson |
| 2,305,462 A | 12/1942 | Wolf |
| 2,453,862 A | 11/1948 | Peter |
| 3,874,388 A | 4/1975 | King et al. |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein et al. |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |

(Continued)

FOREIGN PATENT DOCUMENTS

| | | |
|---|---|---|
| DE | 10028155 A1 | 12/2000 |
| EP | 0283661 | 9/1988 |

(Continued)

OTHER PUBLICATIONS

U.S. Appl. No. 11/775,771, filed Jul. 10, 2007 in the name of Saadat et al., Non-final Office Action mailed Aug. 27, 2010, pp. 1-39.

(Continued)

*Primary Examiner* — Kevin C Sirmons
*Assistant Examiner* — Edelmira Bosques

(57) ABSTRACT

Complex steerable catheter visualization and tissue manipulation systems and their methods of use are disclosed herein. The deployment catheter is articulated using various steering mechanisms. Tissue visualization is accomplished from the visualization hood at the distal end of the deployment catheter, the hood having an ability to expand and other features to facilitate visualization and articulation at the tissue surface.

6 Claims, 35 Drawing Sheets

(56) References Cited

U.S. PATENT DOCUMENTS

| | | | |
|---|---|---|---|
| 4,619,247 A | 10/1986 | Inoue et al. | |
| 4,676,258 A | 6/1987 | Inokuchi et al. | |
| 4,681,093 A | 7/1987 | Ono et al. | |
| 4,709,698 A | 12/1987 | Johnston et al. | |
| 4,710,192 A | 12/1987 | Liotta et al. | |
| 4,727,418 A | 2/1988 | Kato et al. | |
| 4,784,133 A | 11/1988 | Mackin | |
| 4,848,323 A | 7/1989 | Marijnissen et al. | |
| 4,911,148 A | 3/1990 | Sosnowski et al. | |
| 4,914,521 A | 4/1990 | Adair | |
| 4,943,290 A | 7/1990 | Rexroth et al. | |
| 4,950,285 A | 8/1990 | Wilk | |
| 4,957,484 A * | 9/1990 | Murtfeldt | 604/540 |
| 4,961,738 A | 10/1990 | Mackin | |
| 4,976,710 A | 12/1990 | Mackin | |
| 4,991,578 A | 2/1991 | Cohen | |
| 4,994,069 A | 2/1991 | Ritchart et al. | |
| 4,998,916 A | 3/1991 | Hammerslag et al. | |
| 4,998,972 A | 3/1991 | Chin et al. | |
| 5,047,028 A | 9/1991 | Qian | |
| 5,057,106 A | 10/1991 | Kasevich et al. | |
| 5,090,959 A | 2/1992 | Samson et al. | |
| 5,123,428 A | 6/1992 | Schwarz | |
| RE34,002 E | 7/1992 | Adair | |
| 5,156,141 A | 10/1992 | Krebs et al. | |
| 5,171,259 A | 12/1992 | Inoue | |
| 5,281,238 A | 1/1994 | Chin et al. | |
| 5,282,827 A | 2/1994 | Kensey et al. | |
| 5,306,234 A | 4/1994 | Johnson | |
| 5,313,943 A | 5/1994 | Houser et al. | |
| 5,330,496 A | 7/1994 | Alferness | |
| 5,334,159 A | 8/1994 | Turkel | |
| 5,334,193 A | 8/1994 | Nardella | |
| 5,336,252 A | 8/1994 | Cohen | |
| 5,339,800 A | 8/1994 | Wilta et al. | |
| 5,348,554 A | 9/1994 | Imran et al. | |
| 5,353,792 A | 10/1994 | Lubbers et al. | |
| 5,370,647 A | 12/1994 | Graber et al. | |
| 5,373,840 A | 12/1994 | Knighton | |
| 5,375,612 A | 12/1994 | Cottenceau et al. | |
| 5,385,148 A | 1/1995 | Lesh et al. | |
| 5,403,326 A | 4/1995 | Harrison et al. | |
| 5,405,376 A | 4/1995 | Mulier et al. | |
| 5,421,338 A | 6/1995 | Crowley et al. | |
| 5,431,649 A | 7/1995 | Mulier et al. | |
| 5,453,785 A | 9/1995 | Lenhardt et al. | |
| 5,462,521 A | 10/1995 | Brucker et al. | |
| 5,471,515 A | 11/1995 | Fossum et al. | |
| 5,498,230 A | 3/1996 | Adair | |
| 5,505,730 A | 4/1996 | Edwards | |
| 5,515,853 A | 5/1996 | Smith et al. | |
| 5,527,338 A | 6/1996 | Purdy | |
| 5,549,603 A | 8/1996 | Feiring | |
| 5,558,619 A | 9/1996 | Kami et al. | |
| 5,571,088 A | 11/1996 | Lennox et al. | |
| 5,575,756 A | 11/1996 | Karasawa et al. | |
| 5,575,810 A | 11/1996 | Swanson et al. | |
| 5,584,872 A | 12/1996 | LaFontaine et al. | |
| 5,591,119 A | 1/1997 | Adair | |
| 5,593,405 A | 1/1997 | Osypka | |
| 5,593,422 A | 1/1997 | Muijs Van de Moer et al. | |
| 5,593,424 A | 1/1997 | Northrup, III | |
| 5,672,153 A | 9/1997 | Lax et al. | |
| 5,676,693 A | 10/1997 | LaFontaine | |
| 5,681,308 A | 10/1997 | Edwards et al. | |
| 5,695,448 A | 12/1997 | Kimura et al. | |
| 5,697,281 A | 12/1997 | Eggers et al. | |
| 5,697,882 A | 12/1997 | Eggers et al. | |
| 5,709,224 A | 1/1998 | Behl et al. | |
| 5,713,907 A | 2/1998 | Hogendijk et al. | |
| 5,713,946 A | 2/1998 | Ben-Haim | |
| 5,716,321 A | 2/1998 | Kerin et al. | |
| 5,722,403 A | 3/1998 | McGee et al. | |
| 5,725,523 A | 3/1998 | Mueller | |
| 5,746,747 A | 5/1998 | McKeating | |
| 5,749,846 A | 5/1998 | Edwards et al. | |
| 5,749,890 A | 5/1998 | Shaknovich | |
| 5,754,313 A | 5/1998 | Pelchy et al. | |
| 5,766,137 A | 6/1998 | Omata | |
| 5,769,846 A | 6/1998 | Edwards et al. | |
| 5,792,045 A | 8/1998 | Adair | |
| 5,797,903 A | 8/1998 | Swanson et al. | |
| 5,823,947 A * | 10/1998 | Yoon et al. | 600/207 |
| 5,827,268 A | 10/1998 | Laufer | |
| 5,829,447 A | 11/1998 | Stevens et al. | |
| 5,843,118 A | 12/1998 | Sepetka et al. | |
| 5,848,969 A | 12/1998 | Panescu et al. | |
| 5,860,974 A | 1/1999 | Abele | |
| 5,860,991 A | 1/1999 | Klein et al. | |
| 5,865,791 A | 2/1999 | Whayne et al. | |
| 5,873,815 A | 2/1999 | Kerin et al. | |
| 5,879,366 A | 3/1999 | Shaw et al. | |
| 5,895,417 A | 4/1999 | Pomeranz et al. | |
| 5,897,487 A | 4/1999 | Ouchi | |
| 5,897,553 A | 4/1999 | Mulier et al. | |
| 5,902,328 A | 5/1999 | LaFontaine et al. | |
| 5,904,651 A | 5/1999 | Swanson et al. | |
| 5,908,445 A | 6/1999 | Whayne et al. | |
| 5,925,038 A | 7/1999 | Panescu et al. | |
| 5,928,250 A | 7/1999 | Koike et al. | |
| 5,929,901 A | 7/1999 | Adair et al. | |
| 5,941,845 A | 8/1999 | Tu et al. | |
| 5,944,690 A * | 8/1999 | Falwell et al. | 604/170.03 |
| 5,964,755 A | 10/1999 | Edwards | |
| 5,968,053 A | 10/1999 | Revelas | |
| 5,971,983 A * | 10/1999 | Lesh | 606/41 |
| 5,986,693 A | 11/1999 | Adair et al. | |
| 5,997,571 A | 12/1999 | Farr et al. | |
| 6,004,269 A | 12/1999 | Crowley et al. | |
| 6,012,457 A | 1/2000 | Lesh | |
| 6,024,740 A | 2/2000 | Lesh et al. | |
| 6,027,501 A | 2/2000 | Goble et al. | |
| 6,036,685 A | 3/2000 | Mueller | |
| 6,043,839 A | 3/2000 | Adair et al. | |
| 6,047,218 A | 4/2000 | Whayne et al. | |
| 6,063,077 A | 5/2000 | Schaer | |
| 6,063,081 A | 5/2000 | Mulier et al. | |
| 6,068,653 A | 5/2000 | LaFontaine | |
| 6,071,279 A | 6/2000 | Whayne et al. | |
| 6,071,302 A | 6/2000 | Sinofsky et al. | |
| 6,081,740 A | 6/2000 | Gombrich et al. | |
| 6,086,528 A | 7/2000 | Adair | |
| 6,086,534 A | 7/2000 | Kesten | |
| 6,099,498 A | 8/2000 | Addis | |
| 6,099,514 A | 8/2000 | Sharkey et al. | |
| 6,102,905 A | 8/2000 | Baxter et al. | |
| 6,112,123 A | 8/2000 | Kelleher et al. | |
| 6,115,626 A | 9/2000 | Whayne et al. | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,167,297 A | 12/2000 | Benaron | |
| 6,168,591 B1 | 1/2001 | Sinofsky | |
| 6,168,594 B1 | 1/2001 | LaFontaine et al. | |
| 6,174,307 B1 | 1/2001 | Daniel et al. | |
| 6,178,346 B1 | 1/2001 | Amundson et al. | |
| 6,190,381 B1 | 2/2001 | Olsen et al. | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,263,224 B1 | 7/2001 | West | |

(56) References Cited

U.S. PATENT DOCUMENTS

| | | | |
|---|---|---|---|
| 6,270,492 B1 | 8/2001 | Sinofsky | |
| 6,275,255 B1 | 8/2001 | Adair et al. | |
| 6,290,689 B1 | 9/2001 | Delaney et al. | |
| 6,306,081 B1 | 10/2001 | Ishikawa et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 * | 11/2001 | Gambale et al. | 606/41 |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 * | 6/2002 | Farley et al. | 128/898 |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,436,118 B1 | 8/2002 | Kayan | |
| 6,440,061 B1 | 8/2002 | Wenner et al. | |
| 6,440,119 B1 | 8/2002 | Nakada et al. | |
| 6,458,151 B1 | 10/2002 | Saltiel | |
| 6,464,697 B1 | 10/2002 | Edwards et al. | |
| 6,474,340 B1 | 11/2002 | Vaska et al. | |
| 6,475,223 B1 | 11/2002 | Werp et al. | |
| 6,478,769 B1 | 11/2002 | Parker | |
| 6,482,162 B1 | 11/2002 | Moore | |
| 6,484,727 B1 | 11/2002 | Vaska et al. | |
| 6,485,489 B2 | 11/2002 | Teirstein et al. | |
| 6,488,671 B1 | 12/2002 | Constantz et al. | |
| 6,494,902 B2 | 12/2002 | Hoey et al. | |
| 6,497,705 B2 | 12/2002 | Comben | |
| 6,500,174 B1 | 12/2002 | Maguire et al. | |
| 6,502,576 B1 | 1/2003 | Lesh | |
| 6,514,249 B1 | 2/2003 | Maguire et al. | |
| 6,517,533 B1 | 2/2003 | Swaminathan | |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 | 4/2003 | Hassett et al. | |
| 6,544,195 B2 | 4/2003 | Wilson et al. | |
| 6,547,780 B1 | 4/2003 | Sinofsky | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,572,609 B1 | 6/2003 | Farr et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 | 8/2003 | Sinofsky et al. | |
| 6,613,062 B1 | 9/2003 | Leckrone et al. | |
| 6,622,732 B2 | 9/2003 | Constantz | |
| 6,626,855 B1 | 9/2003 | Weng et al. | |
| 6,626,900 B1 | 9/2003 | Sinofsky et al. | |
| 6,635,070 B2 * | 10/2003 | Leeflang et al. | 606/200 |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. | |
| 6,682,526 B1 | 1/2004 | Jones et al. | |
| 6,689,128 B2 | 2/2004 | Sliwa, Jr. et al. | |
| 6,692,430 B2 | 2/2004 | Adler | |
| 6,701,581 B2 | 3/2004 | Senovich et al. | |
| 6,701,931 B2 | 3/2004 | Sliwa, Jr. et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa, Jr. et al. | |
| 6,730,063 B2 | 5/2004 | Delaney et al. | |
| 6,736,810 B2 | 5/2004 | Hoey et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa, Jr. et al. | |
| 6,849,073 B2 | 2/2005 | Hoey et al. | |
| 6,858,005 B2 | 2/2005 | Ohline et al. | |
| 6,858,026 B2 | 2/2005 | Sliwa, Jr. et al. | |
| 6,863,668 B2 | 3/2005 | Gillespie et al. | |
| 6,866,651 B2 | 3/2005 | Constantz | |
| 6,887,237 B2 | 5/2005 | McGaffigan | |
| 6,892,091 B1 | 5/2005 | Ben-Haim et al. | |
| 6,896,690 B1 | 5/2005 | Lambrecht et al. | |
| 6,899,672 B2 | 5/2005 | Chin et al. | |
| 6,915,154 B1 | 7/2005 | Docherty et al. | |
| 6,916,284 B2 | 7/2005 | Moriyama | |
| 6,923,805 B1 | 8/2005 | LaFontaine et al. | |
| 6,929,010 B2 | 8/2005 | Vaska et al. | |
| 6,932,809 B2 | 8/2005 | Sinofsky | |
| 6,939,348 B2 | 9/2005 | Malecki et al. | |
| 6,942,657 B2 | 9/2005 | Sinofsky et al. | |
| 6,949,095 B2 | 9/2005 | Vaska et al. | |
| 6,953,457 B2 | 10/2005 | Farr et al. | |
| 6,955,173 B2 | 10/2005 | Lesh | |
| 6,962,589 B2 | 11/2005 | Mulier et al. | |
| 6,971,394 B2 | 12/2005 | Sliwa, Jr. et al. | |
| 6,974,464 B2 | 12/2005 | Quijano et al. | |
| 6,979,290 B2 | 12/2005 | Mourlas et al. | |
| 6,982,740 B2 | 1/2006 | Adair et al. | |
| 6,984,232 B2 | 1/2006 | Vanney et al. | |
| 6,994,094 B2 | 2/2006 | Schwartz | |
| 7,019,610 B2 | 3/2006 | Creighton, IV et al. | |
| 7,025,746 B2 | 4/2006 | Tal | |
| 7,030,904 B2 | 4/2006 | Adair et al. | |
| 7,041,098 B2 | 5/2006 | Farley et al. | |
| 7,042,487 B2 | 5/2006 | Nakashima | |
| 7,044,135 B2 | 5/2006 | Lesh | |
| 7,052,493 B2 | 5/2006 | Vaska et al. | |
| 7,090,683 B2 | 8/2006 | Brock et al. | |
| 7,118,566 B2 | 10/2006 | Jahns | |
| 7,156,845 B2 | 1/2007 | Mulier et al. | |
| 7,163,534 B2 | 1/2007 | Brucker et al. | |
| 7,166,537 B2 | 1/2007 | Jacobsen et al. | |
| 7,169,144 B2 | 1/2007 | Hoey et al. | |
| 7,186,214 B2 | 3/2007 | Ness | |
| 7,207,984 B2 | 4/2007 | Farr et al. | |
| 7,217,268 B2 | 5/2007 | Eggers et al. | |
| 7,242,832 B2 | 7/2007 | Carlin et al. | |
| 7,247,155 B2 | 7/2007 | Hoey et al. | |
| 7,261,711 B2 | 8/2007 | Mulier et al. | |
| 7,263,397 B2 | 8/2007 | Hauck et al. | |
| 7,276,061 B2 | 10/2007 | Schaer et al. | |
| 7,309,328 B2 | 12/2007 | Kaplan et al. | |
| 7,416,552 B2 | 8/2008 | Paul et al. | |
| 7,435,248 B2 | 10/2008 | Taimisto et al. | |

(56) References Cited

U.S. PATENT DOCUMENTS

| | | |
|---|---|---|
| 7,527,625 B2 | 5/2009 | Knight et al. |
| 7,534,204 B2 | 5/2009 | Starksen et al. |
| 7,569,052 B2 | 8/2009 | Phan et al. |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 8,131,350 B2 | 3/2012 | Saadat et al. |
| 8,137,333 B2 | 3/2012 | Saadat et al. |
| 2001/0005789 A1 | 6/2001 | Root et al. |
| 2001/0020126 A1 | 9/2001 | Swanson et al. |
| 2001/0031912 A1 | 10/2001 | Adler |
| 2001/0039416 A1 | 11/2001 | Moorman et al. |
| 2001/0047136 A1 | 11/2001 | Domanik et al. |
| 2001/0047184 A1 | 11/2001 | Connors |
| 2001/0052930 A1 | 12/2001 | Adair et al. |
| 2002/0004644 A1 | 1/2002 | Koblish |
| 2002/0026145 A1 | 2/2002 | Bagaoisan et al. |
| 2002/0054852 A1 | 5/2002 | Cate |
| 2002/0065455 A1 | 5/2002 | Ben-Haim et al. |
| 2002/0068853 A1 | 6/2002 | Adler |
| 2002/0080248 A1 | 6/2002 | Adair et al. |
| 2002/0087166 A1 | 7/2002 | Brock et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0009085 A1 | 1/2003 | Arai et al. |
| 2003/0036698 A1 | 2/2003 | Kohler et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky et al. |
| 2003/0220574 A1 | 11/2003 | Markus et al. |
| 2003/0222325 A1 | 12/2003 | Jacobsen et al. |
| 2004/0006333 A1 | 1/2004 | Arnold et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0097788 A1 | 5/2004 | Mourlas et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215180 A1 | 10/2004 | Starkebaum et al. |
| 2004/0215183 A1 | 10/2004 | Hoey et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1* | 6/2005 | Starksen et al. ............. 600/109 |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0184048 A1 | 8/2006 | Saadat |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |

(56) References Cited

U.S. PATENT DOCUMENTS

| | | | |
|---|---|---|---|
| 2008/0033290 | A1 | 2/2008 | Saadat et al. |
| 2008/0057106 | A1 | 3/2008 | Erickson et al. |
| 2008/0058590 | A1 | 3/2008 | Saadat et al. |
| 2008/0058650 | A1 | 3/2008 | Saadat et al. |
| 2008/0058836 | A1 | 3/2008 | Moll et al. |
| 2008/0097476 | A1 | 4/2008 | Peh et al. |
| 2008/0183081 | A1 | 7/2008 | Lys et al. |
| 2008/0188759 | A1 | 8/2008 | Saadat et al. |
| 2008/0214889 | A1 | 9/2008 | Saadat et al. |
| 2008/0228032 | A1 | 9/2008 | Starksen et al. |
| 2008/0275300 | A1 | 11/2008 | Rothe et al. |
| 2008/0287790 | A1 | 11/2008 | Li |
| 2008/0287805 | A1 | 11/2008 | Li |
| 2009/0030412 | A1 | 1/2009 | Willis et al. |
| 2009/0054803 | A1 | 2/2009 | Saadat et al. |
| 2009/0062790 | A1 | 3/2009 | Malchano et al. |
| 2009/0076489 | A1 | 3/2009 | Welches et al. |
| 2009/0076498 | A1 | 3/2009 | Saadat et al. |
| 2009/0143640 | A1 | 6/2009 | Saadat et al. |
| 2009/0264727 | A1 | 10/2009 | Markowitz et al. |
| 2009/0267773 | A1 | 10/2009 | Markowitz et al. |
| 2010/0004506 | A1 | 1/2010 | Saadat |
| 2010/0004661 | A1 | 1/2010 | Verin et al. |
| 2011/0060227 | A1 | 3/2011 | Saadat |
| 2011/0060298 | A1 | 3/2011 | Saadat |
| 2011/0144576 | A1 | 6/2011 | Rothe et al. |
| 2012/0016221 | A1 | 1/2012 | Saadat et al. |

FOREIGN PATENT DOCUMENTS

| | | |
|---|---|---|
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

U.S. Appl. No. 11/828,267, filed Jul. 25, 2007 in the name of Saadat et al., final Office Action mailed Sep. 16, 2010, pp. 1-37.
U.S. Appl. No. 11/763,399, filed Jun 14, 2007 in the name of Saadat et al., non-final Office Action mailed Apr. 11, 2011, pp. 1-45.
U.S. Appl. No. 12/499,011, filed Jul. 7, 2009 in the name of Rothe et al., non-final Office Action mailed Apr. 12, 2011, pp. 1-42.
U.S. Appl. No. 12/367,019, filed Feb. 6, 2009 in the name of Miller et al., non-final Office Action mailed Apr. 22, 2011, pp. 1-39.
U.S. Appl. No. 11/959,158, filed Dec. 18, 2007 in the name of Saadat et al., non-final Office Action mailed Apr. 25, 2011, pp. 1-49.
U.S. Appl. No. 11/848,532, filed Aug. 31, 2007 in the name of Saadat et al., non-final Office Action mailed Apr. 26, 2011, pp. 1-30.
U.S. Appl. No. 11/828,281, filed Jul. 25, 2007 in the name of Peh et al., non-final Office Action mailed Apr. 27, 2011, pp. 1-30.
U.S. Appl. No. 11/961,950, filed Dec. 20, 2007 in the name of Saadat et al., non-final Office Action mailed May 9, 2011, pp. 1-47.
U.S. Appl. No. 11/961,995, filed Dec. 20, 2007 in the name of Saadat et al., non-final Office Action mailed May 9, 2011, pp . 1-40.
U.S. Appl. No. 11/962,029, filed Dec. 20, 2007 in the name of Saadat et al., non-final Office Action mailed May 9, 2011, pp. 1-46.
U.S. Appl. No. 11/828,267, filed Jul. 25, 2007 in the name of Saadat et al., non-final Office Action mailed May 11, 2011, pp.
Japanese Patent Application No. 2009-500630 filed Mar. 16, 2007 in the name of Voyage Medical, Inc., Office Action mailed Apr. 27, 2011, 1-3.
U.S. Appl. No. 11/775,771, filed Jul 10, 2007 in the name of Saadat et al., final Office Action mailed May 12, 2011, pp. 1-21.
U.S. Appl. No. 11/877,386, filed Oct. 23, 2007 in the name of Saadat et al., non-final Office Action mailed May 20, 2011, pp. 1-44.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2607 in the name of Saadat et al., non-final Office Action mailed May 23, 2011, pp. 1-69.
U.S. Appl. No. 12/323,281, filed Nov. 25, 2008 in the name of Saadat et al., non-final Office Action mailed Jun. 7, 2011, pp. 1-35.
European Patent Application No. 06734083.6 filed Jan. 30, 2006 in the name of Voyage Medical, Inc., Office Action mailed Nov. 12, 2010.
U.S. Appl. No. 12/947,198, filed Nov. 16, 2010 in the name of Saadat, non-final Office Action mailed Feb. 18, 2011.
U.S. Appl. No. 12/947,246, filed Nov. 16, 2006 in the name of Saadat, Notice of Allowance mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/259,498, filed Oct. 25, 2005 in the name of Saadat, Notice of Allowance mailed Nov. 15, 2010.
U.S. Appl. No. 11/560,742, filed Nov. 16, 2006 in the name of Saadat, Notice of Allowance mailed Nov. 15, 2010.
U.S. Appl. No. 12/464,800, filed May 12, 2009 in the name of Peh et al., non-final Office Action mailed Nov. 24, 2010.
U.S. Appl. No. 11/848,429, filed Aug. 31, 2007 in the name of Peh et al., non-final Office Action mailed Nov. 24, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.
U.S. Appl. No. 11/560,732, filed Nov. 16, 2006 in the name of Saadat, Notice of Allowance mailed Feb. 3, 2011.
U.S. Appl. No. 12/026,455, filed Feb. 5, 2008 in the name of Saadat et al., non-final Office Action mailed Dec. 27, 2010.
European Patent Application No. 06734083.6 filed Jan. 30, 2006 in the name of Saadat et al., Examination Communication mailed May 18, 2010.

(56) References Cited

OTHER PUBLICATIONS

European Patent Application No. 07841754.0 filed Aug. 31, 2007 in the name of Saadat at at., Supplemental European Search Report mailed Jun. 30, 2010.
European Patent Application No. 08746822.9 filed Apr. 24, 2008 in the name of Rothe at al., European Search Report mailed Mar. 29, 2010.
European Patent Application No. 08746822.9 filed Apr. 24, 2008 in the name of Rothe et al., Office Action mailed Jul. 13, 2010.
U.S. Appl. No. 11/259,498, filed Oct. 25, 2005 in the name of Saadat et al., Non-final Office Action mailed Feb. 25, 2010.
U.S. Appl. No. 11/560,742, filed Nov. 16, 2006 in the name of Saadat, Non-final Office Action mailed Jun. 10, 2010.
U.S. Appl. No. 11/687,597, filed Mar. 16, 2007 in the name of Saadat et al., Non-final Office Action mailed Jul. 21, 2010.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Futura Publishing Co., Armonk, NY.
Willkampf, Radiofrequency Ablation with a Cooled Porous Electrode Catheter. JACC, vol. 11, No. 2, p. 17A, 1988.
Avitall, A Catheter System to Ablate Atrial Fibrillation in a Sterile Pericarditis Dog Model, PACE, vol. 17, p. 774, 1994.
Avitall, Right-Sided Driven Atrial Fibrillation in a Sterile Pericarditis Dog Model, PACE, vol. 17, p. 774, 1994.
Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.
Baker, Nonpharmacologic Approaches to the Treatment of Atrial Fibrillation and Atrial Flutter, J. Cardiovasc. Electrophysiol., vol. 6, pp. 972-978, 1995.
Bhakta, Principles of Electroanatomic Mapping, Indian Pacing & Electrophysiol J., vol. 8, No. 1, pp. 32-50, 2008.
Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.
Bredikis, Surgery of Tachyarrhythmia: Intracardiac Closed Heart Cryoablation, PACE, vol. 13, pp. 1980-1984, 1990.
Cox, Cardiac Surgery for Arrhythmias, J. Cardiovasc. Electrophysiol., vol. 15, pp. 250-262, 2004.
Cox, Five-Year Experience With the Maze Procedure for Atrial Fibrillation, Ann. Thorac. Surg., vol. 56, pp. 814-824, 1993.
Cox, Modification of the Maze Procedure for Atrial Flutter and Atrial Fibrillation, J. Thorac. Cardiovasc. Surg., vol. 110, pp. 473-484, 1995.
Cox, The Status of Surgery for Cardiac Arrhythmias, Circulation, vol. 71, pp. 413-417, 1985.
Cox, The Surgical Treatment of Atrial Fibrillation, J. Thorac Cardiovasc. Surg., vol. 101, pp. 584-592, 1991.
Elvan, Replication of the "Maze" Procedure by Radiofrequency Catheter Ablation Reduces the Ability to Induce Atrial Fibrillation, PACE, vol. 17, p. 774, 1994.
Elvan, Radiofrequency Catheter Ablation (RFCA) of the Atria Effectively Abolishes Pacing Induced Chronic Atrial Fibrillation, PACE, vol. 18, p. 856, 1995.
Elvan, Radiofrequency Catheter Ablation of the Atria Reduces Inducibility and Duration of Atrial Fibrillation in Dogs, Circulation, vol. 91, pp. 2235-2244, 1995.
European Patent Application No. 06734083.6 filed Jan. 30, 2006 in the name of Saadat et al., extended European Search Report mailed Jul. 1, 2009.
European Patent Application No. 06734083.6 filed Jan. 30, 2006 in the name of Saadat et al., office action mailed Oct. 23, 2009.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy Via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/828,267, filed Jul. 25, 2007 in the name of Saadat et al., Non-final Office Action mailed Jan. 14, 2010.
U.S. Appl. No. 12/117,665, filed May 8, 2008 in the name of Saadat et al., Non-final Office Action mailed Jun. 8, 2009.
Willkampf, Radiofrequency Ablation with a Cooled Porous Electrode Catheter, JACC, vol. 11, No. 2, p. 17A, 1988.

* cited by examiner

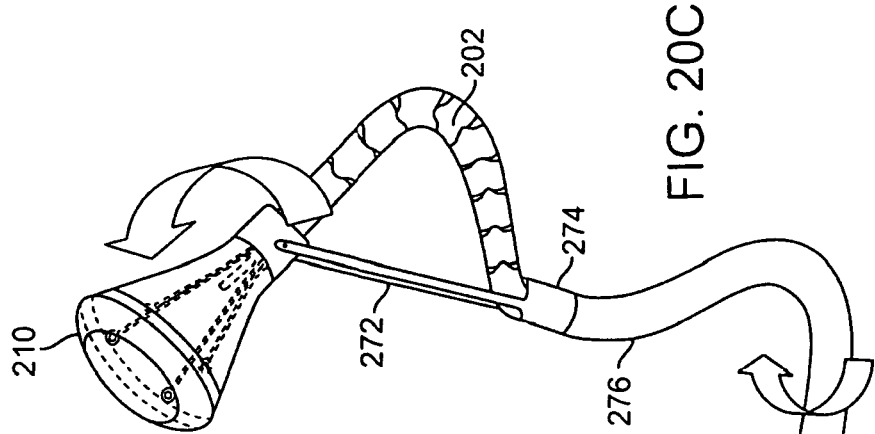
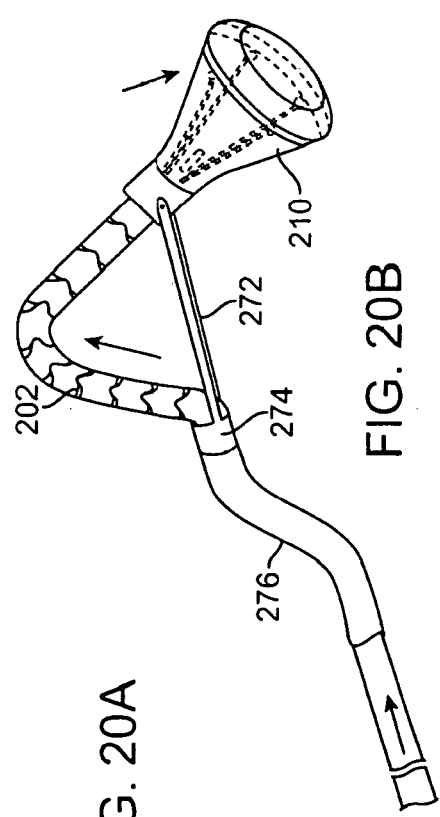
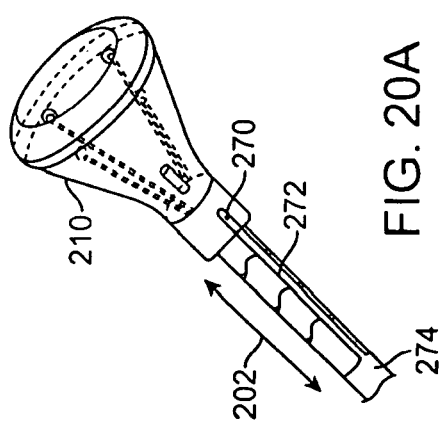
FIG. 20A
FIG. 20B
FIG. 20C

COMPLEX SHAPE STEERABLE TISSUE VISUALIZATION AND MANIPULATION CATHETER

CROSS-REFERENCE TO RELATED APPLICATIONS

This application claims the benefit of priority to U.S. Prov. Pat. App. 60/916,640 filed May 8, 2007, which is incorporated herein by reference in its entirety.

FIELD OF THE INVENTION

The present invention relates generally to catheters having imaging and manipulation features for intravascularly accessing regions of the body.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. No. 5,895,417; 5,941, 845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. Without real-time visualization, it is difficult to reposition devices to another area that requires transmural lesion ablation. The absence of real-time visualization also poses the risk of incorrect placement and ablation of critical structures such as sinus node tissue which can lead to fatal consequences.

BRIEF SUMMARY OF THE INVENTION

A tissue imaging system which is able to provide real-time in vivo access to and images of tissue regions within body lumens such as the heart through opaque media such as blood and which also provides instruments for therapeutic procedures is provided by the invention.

The tissue-imaging apparatus relates to embodiments of a device and method to provide real-time images in vivo of tissue regions within a body lumen such as a heart, which is filled with blood flowing dynamically through it. Such an apparatus may be utilized for many procedures, e.g., mitral valvuloplasty, left atrial appendage closure, arrhythmia ablation (such as treatment for atrial fibrillation), transseptal access and patent foramen ovale closure among other procedures. Further details of such a visualization catheter and methods of use are shown and described in U.S. Pat. Pub. 2006/0184048 A1, which is incorporated herein by reference in its entirety.

Generally, the embodiments of a tissue imaging and manipulation device depicted in the present invention meet the challenge and solve the problem of accessing regions of the body which are typically difficult to access. The design and control of the catheter shaft and the distal tip of the device as disclosed here provide a device uniquely capable of accessing a region such as the human heart, which is a region not only difficult to access, but which also has continuous blood flow. The blood flow provides a barrier to visualizing the local tissue, which in turn makes any manipulation at the local tissue nearly impossible. The unique elements that form the catheter shaft and the distal tip of the device, including the separate control of the shaft and tip and several optional modes of manipulation of either or both, provide for a device adaptable to addressing the challenges inherent in intravascular access and manipulation of heart tissue, and for accomplishing a procedure in any other difficult-to-access region in the body which is bathed in a medium that interferes with visualization.

Blood is continuously flowing through the heart at all times, and as such presents a challenge to direct visualization and subsequent manipulation of heart tissue. The tissue imaging and manipulation apparatus can comprise a delivery catheter or sheath through which a deployment catheter and imaging hood may be advanced for placement against or adjacent to the tissue to be imaged. The deployment catheter can have a fluid delivery lumen through it as well as an imaging lumen within which an optical imaging fiber or electronic imaging assembly may be disposed for imaging tissue. The distal tip of the device is an articulatable tip connected to the catheter shaft, when deployed, the imaging hood within the articulatable tip may be expanded into any number of shapes, e.g., cylindrical, conical as shown, semi-spherical, etc., provided that an open area or field is defined by the imaging hood. The open area of the articulatable tip is the area within which the tissue region of interest may be imaged. The imaging hood may also define an atraumatic contact lip or edge for placement or abutment against the tissue surface in the region of interest. The distal end of the deployment catheter or separate manipulatable catheters within a delivery sheath may be articulated through various controlling mechanisms such as push-pull wires manually or via computer control.

The visualization catheter may also have one or more membranes or layers of a polymeric material which covers at least a portion of the open area. The membrane or layer may be an extension of the deployed hood or it may be a separate structure. In either case, the membrane or layer may define at least one opening which allows for fluid communication between the visualization hood and the fluid environment within which the catheter is immersed.

In operation, after the imaging hood (at the articulatable tip) has been deployed, fluid may be pumped at a positive pressure through the fluid delivery lumen (within the catheter) until the fluid fills the open area completely and displaces any blood from within the open area. When the hood and membrane or layer is pressed against the tissue region to be visualized or treated, the contact between the one or more openings and the tissue surface may help to retain the clear fluid within the hood for visualization. Moreover, the membrane or layer may help to retain the fluid within the hood while also minimizing any fluid leakage therefrom. Additionally, the one or more openings may also provide for direct access to the underlying tissue region to be treated by any number of tools or instruments positioned within the hood at the articulatable tip.

The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be deployed into an expanded shape and retracted within a catheter utilizing various mechanisms. Moreover, an imaging element, such as a CCD/CMOS imaging camera, may be positioned distally or proximally of the imaging hood when collapsed into its low-profile configuration. Such a configuration may reduce or eliminate friction during deployment and retraction as well as increase the available space within the catheter not only for the imaging unit but also for the hood.

In further controlling the flow of the purging fluid within the hood, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood may be maintained for relatively longer periods of time by inhibiting, delaying, or preventing the infusion of surrounding blood into the viewing field.

Accordingly, there is provided a device for visualization and manipulation of difficult-to-reach tissue surfaces in a region of a body having a continuous interfering blood flow comprising a steerable catheter shaft having controls for steering of the shaft in multiple planes. The steering of the catheter and/or sheath may be separately controlled during a procedure so that a proximal steerable section of a catheter shaft can be steered to a target region without manipulation of the distal steerable section. Upon arrival at the target region, slight adjustments and steering of the hood may be articulated (and/or independently) to address the tissue surface or otherwise contact or approach a tissue surface.

The tasks performed by the articulatable hood utilize movement of the catheter shaft, but the movements of the hood and the shaft can be independent in function and control. For example, in order for the hood to contact the tissue surface to flush the region in preparation for imaging, or for making contact with and manipulating the tissue (e.g., forming a lesion around a pulmonary ostium and the like), the catheter shaft may be moved and directed or re-directed to position the hood, then once the catheter shaft has placed the hood in a desirable position, further articulation and control of the hood for cutting or lesion formation or the like can occur. For example, the hood can be articulated to contact the tissue surface and form a suitable seal in order to flush the surface with saline to visualize the tissue at the surface. The hood may have a conforming lip that can be used to make contact with the tissue surface to facilitate any of these tasks or manipulations. At the point where the hood is negotiating its position at the tissue surface, any subsequent adjustments that may need to be made to the positioning of the shaft can be made independently of the movement of the hood, although, where catheter shaft adjustment can facilitate the hood's position relative to the tissue surface, the two control mechanisms can work in concert with each other.

The distal articulatable hood can comprise one or more articulatable units along the hood that are adapted to distal control and that allow the hood to conform to the tissue surface. The articulatable units can comprise multiple steerable leaflets inside a cone-like hood. An articulatable unit can comprise a steerable hood. It may also comprise control members within the hood that allow the practitioner to manipulate the lip that surrounds the hood and the like. The distal articulatable hood can comprise a conforming lip that can be passively steered to contact the tissue surface.

The device can further comprise two or more variations in durometer along the catheter shaft. For example, where there is at least one variation in durometer along the catheter shaft, the variation in durometer can comprise a region of increased flexibility distal to a region of relatively reduced flexibility, so that the distal most end is more flexible and manipulatable.

Where the catheter shaft comprises locking units, the shaft can further comprise an outer sheath to smooth out links in the catheter shaft in the region of the shaft having the locking units.

The catheter shaft can be multi-lumen and comprise multiple pull wires, each pull wire having its own separate access lumen within the catheter shaft. In addition, the device can have a fixed bent sheath over a portion of the catheter shaft to limit the movement of the shaft where the sheath is positioned and define a fixed angle of direction of the shaft at the fixed bend.

A tissue visualization unit adapted to visualizing accessed tissue can be positioned within the articulatable tip or hood. A tissue manipulation unit adapted to manipulating accessed tissue can likewise be positioned within the articulatable tip. A device can have both such units, for optimally imaging and manipulating in the body during a procedure in real-time.

The invention is also a system for intravascularly accessing difficult to access target tissue in a region of the body having continuous interfering blood flow. The system employs a device adapted to visualization and manipulation of the accessed target tissue as just described. The device for the system may have a catheter capable of flushing the target tissue surface at the distal tip so that visualization and manipulation at the surface can occur once the tip is in contact with the tissue surface, and both a unit for visualizing the tissue surface and manipulating tissue at the tissue surface positioned within the articulatable tip. Alternatively, the system can be just for visualization of the tissue surface, in which case it will only have the visualization mechanism.

Also contemplated are methods of visualizing or manipulating difficult-to-access target tissue in a region of a body having continuous interfering blood flow. One method comprises introducing into a main artery in a patient a device described herein having the steerable catheter component and the distal attached articulatable tip component. The controls for the catheter shaft may include pull wires, locking units and variations in durometer of the shaft, etc. The articulatable hood is expandable upon arrival of the device at a target region in a body, and the hood is capable of expansion to a greater diameter than the catheter shaft.

Further refinements to the steering and control of the proximal steerable section of the catheter can be accomplished a number of ways. The catheter shaft may have a multi-lumen extrusion through which pullwires can be placed for controlling the shaft using keyhole lumens to refine the articulation of the steerable segment of the catheter. Accordingly, using these elements, the proximal steerable section is able to articulate within multiple planes relative to a longitudinal axis of the catheter.

The proximal steerable section can be configured using a steering guide that travels along a steering actuator. The steering guide is a rigid member and the steering actuator can slide along it to affect a transition of the steerable segment. This embodiment can further comprise pullwires that travel with the steering guide.

Another configuration of the apparatus that facilitates complex manipulation of both the steerable segment and the distal segment (including the hood) is a push steering mechanism in which a hinged bar aligns with the base of the distal segment and connects to the base of a region in the steerable segment that also connects to a slidable sheath located more proximally. The hinged bars control movement of the hood by creating a curve in the steerable segment that directs push control to the hood. The hinged bar guides and limits the movement of the steerable section in order to direct the position of the distal hood towards a target region. In this way the distal steerable section is adapted to articulate within one or more planes relative to a longitudinal axis of the proximal steerable section.

The embodiments directed towards complex steering, manipulation and control of the steerable sections can include that the proximal and distal steerable sections each comprise a plurality of serially aligned links which are selected from pin links, bump links, ring links, one-way links, and four-way links, etc. In addition, the proximal and distal steerable sections can each comprise a durometer different from one another. In yet another embodiment, the proximal section can comprise a steerable retro-flexing introducer sheath that directs the distal steerable section to articulate within one or more planes relative to a longitudinal axis of the proximal steerable section.

Another variation is directed towards optimized and complicated visualization of the target tissue using the visualization hood. The distal steerable section can comprise an expandable visualization member, which can be balloon expandable. Imaging elements can reside within the expanded visualization member. The expandable imaging member can be compressed for delivery in the catheter and then expanded upon release from the distal end of the catheter.

The distal steerable section can comprise an expandable anchoring member and an ablation optical source, positioned distal of an expandable visualization member. The ablation optical source can be placed in the visualization member for ablating local tissue. The anchoring member can serve to anchor the distal end at the target region so that the ablation can be directed to specific target locations. Yet another embodiment includes that the distal steerable section comprising an infrared endoscope.

The proximal and distal sections can be controlled by a handle at the proximal end of the catheter for driving the proximal and distal steering segments, and for supporting a variety of tools. The tools can be selected from a syringe, a fiberscope, a needle, valves for irrigation port, imaging elements, and valves for passing tools, for example. Pullwires can be connected to a steering lever on the handle for providing tension through the pullwires to the steerable sections of the catheter. For example, a lever on the handle can be turned to provide tension on the pullwires, which in turn controls the movement of the proximal steerable section or the distal steerable section.

Also included are methods of accessing difficult-to-reach target tissue in a region of a body having continuous interfering blood flow by articulating the proximal steerable section within multiple planes relative to a longitudinal axis of the catheter guided by keyhole lumens, and articulating the distal steerable section within one or more planes relative to a longitudinal axis of the proximal steerable section. Accordingly, the distal hood can contact difficult to reach target tissue, for example, using complex curves generated with the proximal steerable segment so that the distal segment (the hood) can contact the target tissue perpendicularly, thus providing optimum contact of the hood with the tissue. Visualizing the target tissue within an open area through the transparent fluid can be accomplished if the visualization hood is flushed with saline or other clear fluid so that the blood is cleared providing an unobstructed visualization at the region. Processes such as ablation, or marking can occur using the distal hood of at least a portion of the target tissue within the open area that has been cleared of blood.

BRIEF DESCRIPTION OF THE DRAWINGS

FIGS. 20A to 20C depict a push steering mechanism used to control the proximal steerable section and articulate the distal hood about the hinges of the push steering mechanism.

DETAILED DESCRIPTION OF THE INVENTION

The tissue-imaging and manipulation apparatus of the invention is able to provide real-time images in vivo of tissue regions within a body lumen such as a heart, which are filled with blood flowing dynamically through the region. The apparatus is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation (such as for treating atrial fibrulation), among other procedures. Disclosure and information regarding tissue visualization catheters generally which can be applied to the invention are shown and described in further detail in commonly owned U.S. patent application Ser. No. 11/259,498 filed Oct. 25, 2005, and published as U.S. Pat. Pub. 2006/0184048, which is incorporated herein by reference in its entirety. The basic apparatus for visualizing and manipulating tissue upon intravascular access to the target region are depicted in FIGS. 1 to 10. The specific details that permit specific access to difficult-to-access regions such as regions in the heart are depicted in FIGS. 11 to 25.

Figure 1A:
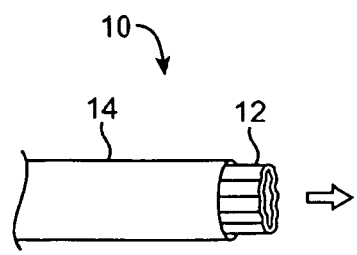
FIG. 1A shows a side view of one variation of a tissue imaging apparatus during deployment from a sheath or delivery catheter.
Figure 1B:
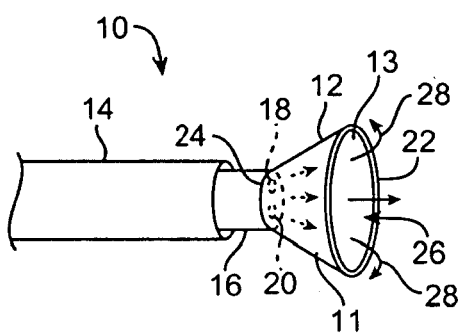
FIG. 1B shows the deployed tissue imaging apparatus of FIG. 1A having an optionally expandable hood or sheath attached to an imaging and/or diagnostic catheter.
Figure 1C:
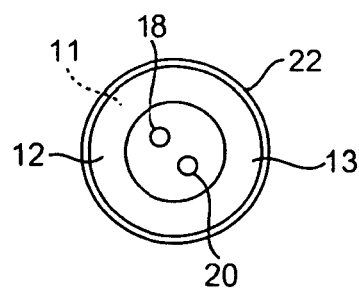
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
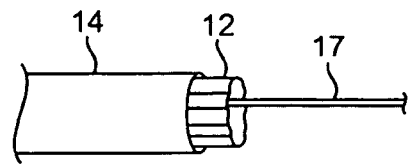
FIGS. 1D to 1F show the apparatus of FIGS. 1A to 1C with an additional lumen, e.g., for passage of a guidewire therethrough.
Figure 1E:
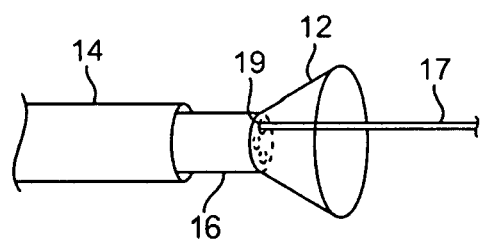
Figure 1F:
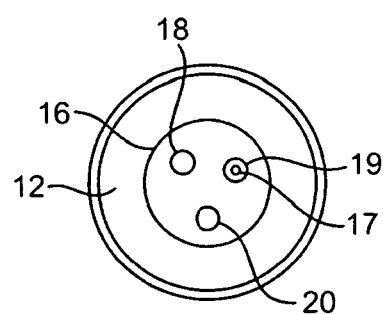

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
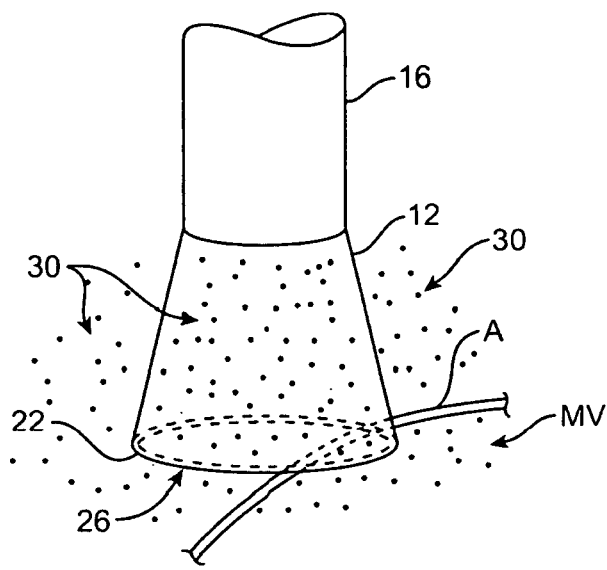
FIGS. 2A and 2B show one example of a deployed tissue imager positioned against or adjacent to the tissue to be imaged and a flow of fluid, such as saline, displacing blood from within the expandable hood.
Figure 2B:
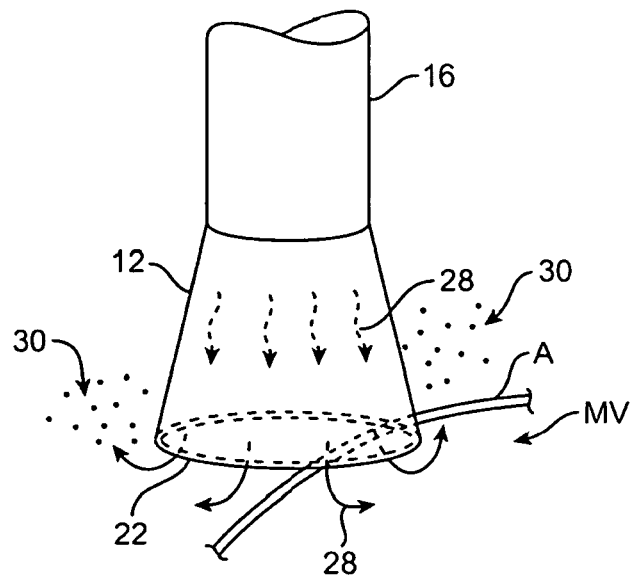

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3A:
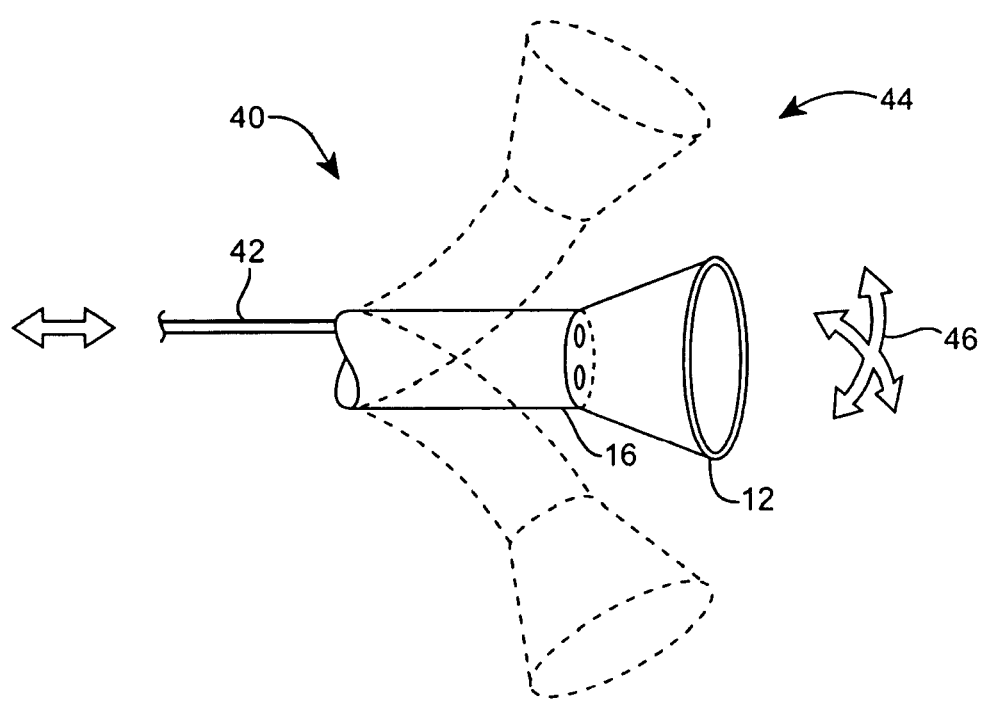
FIG. 3A shows an articulatable imaging assembly which may be manipulated via push-pull wires or by computer control.
Figure 3B:
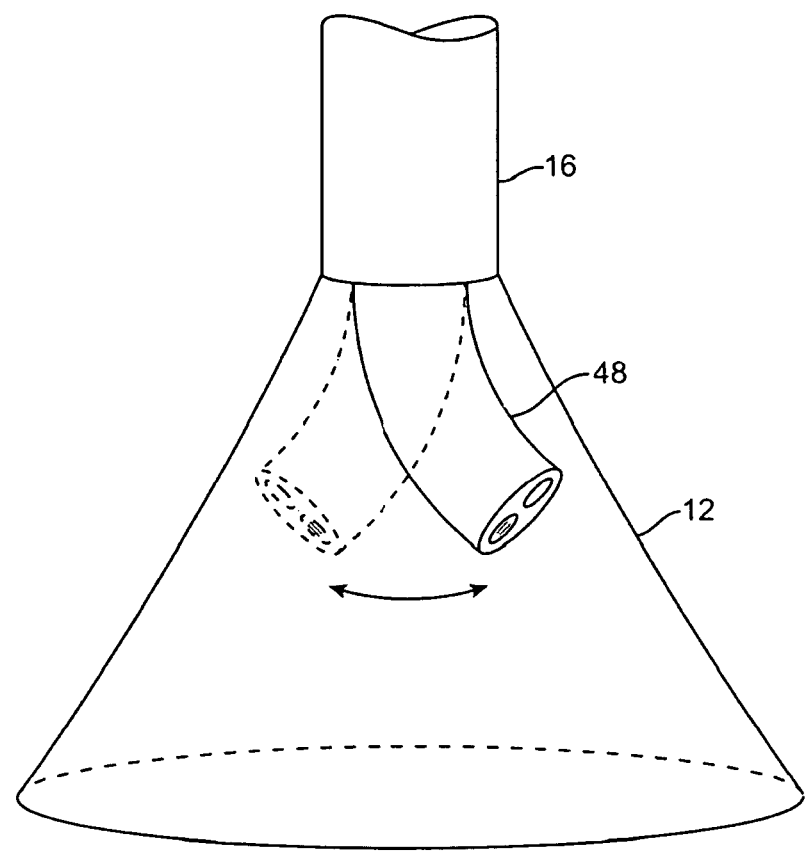
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
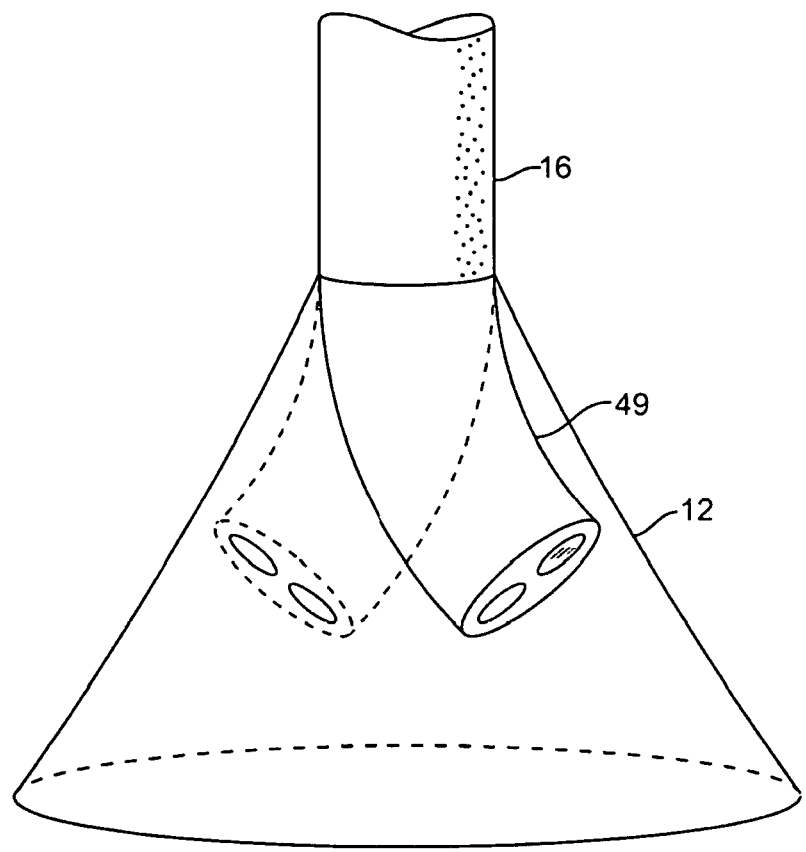

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
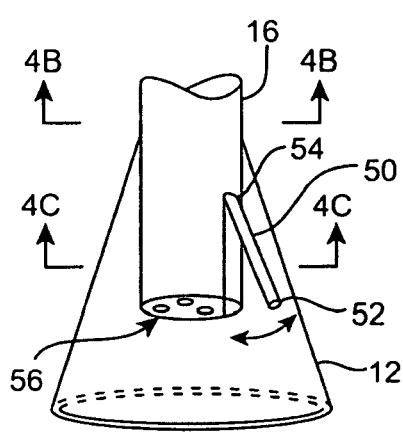
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
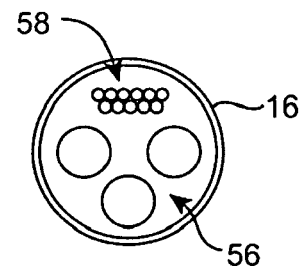
Figure 4C:
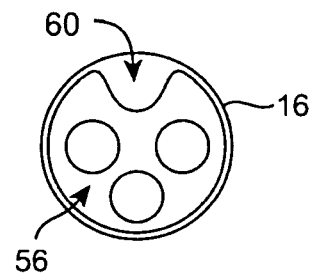

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
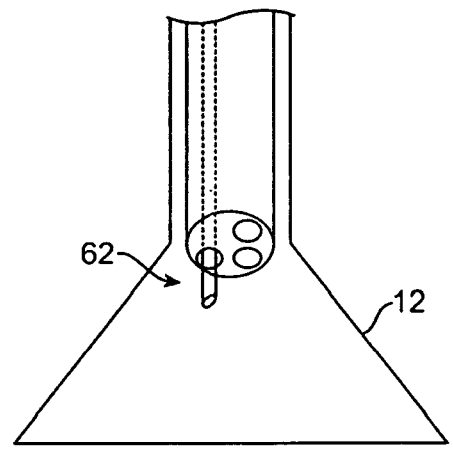
FIGS. 4D and 4E show examples of various visualization imagers which may be utilized within or along the imaging hood.
Figure 4E:
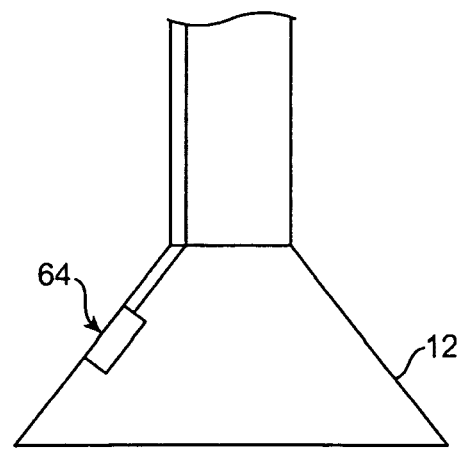

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 5:
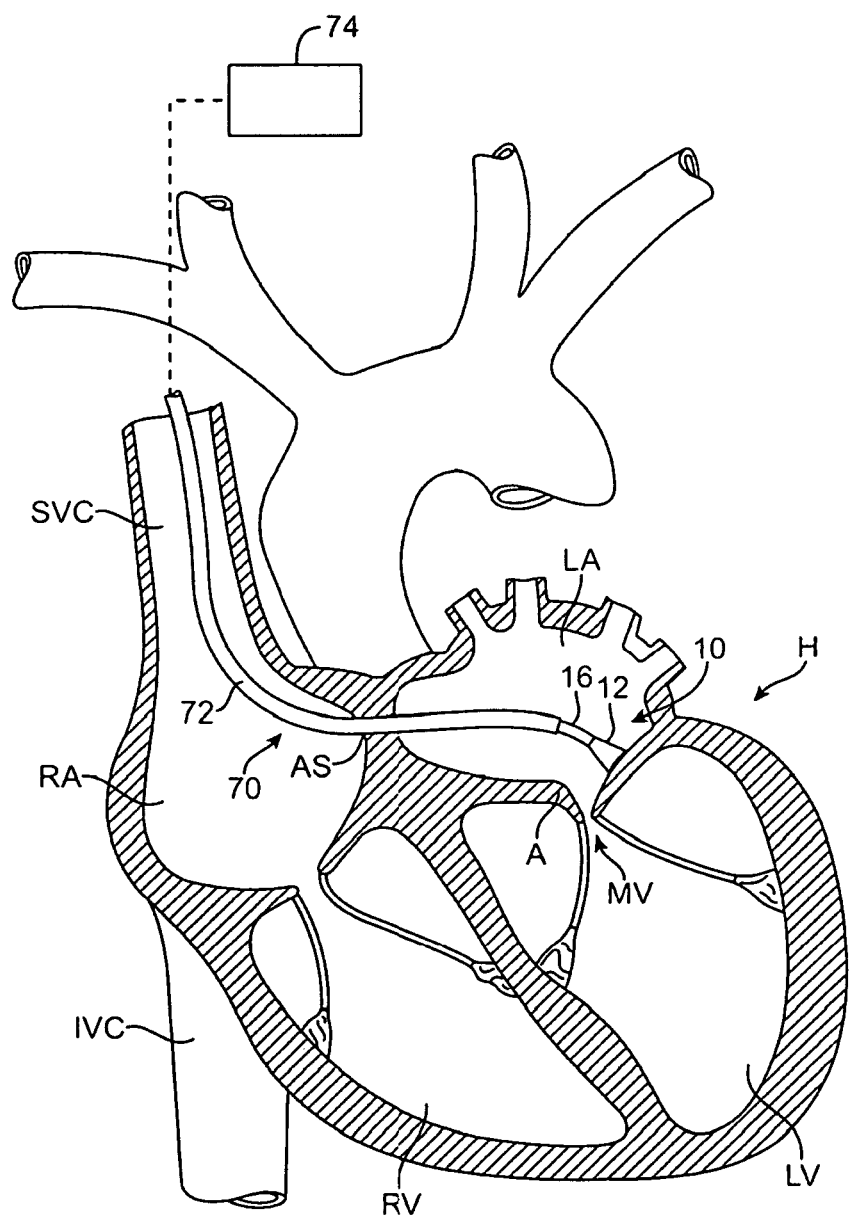
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
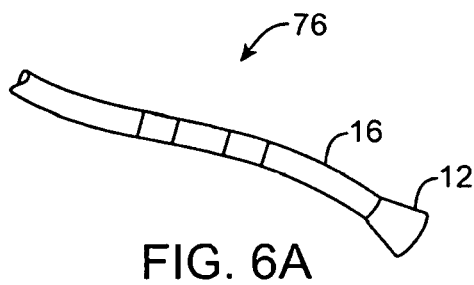
FIGS. 6A to 6C illustrate deployment catheters having one or more optional inflatable balloons or anchors for stabilizing the device during a procedure.
Figure 6B:
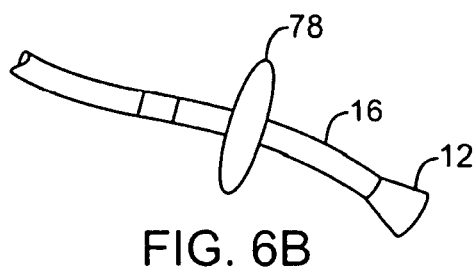
Figure 6C:
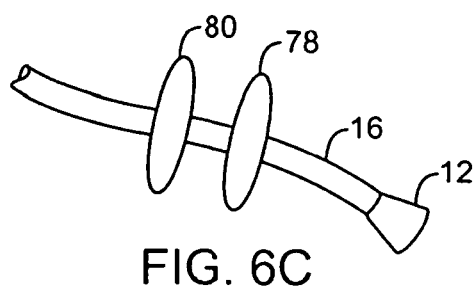

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
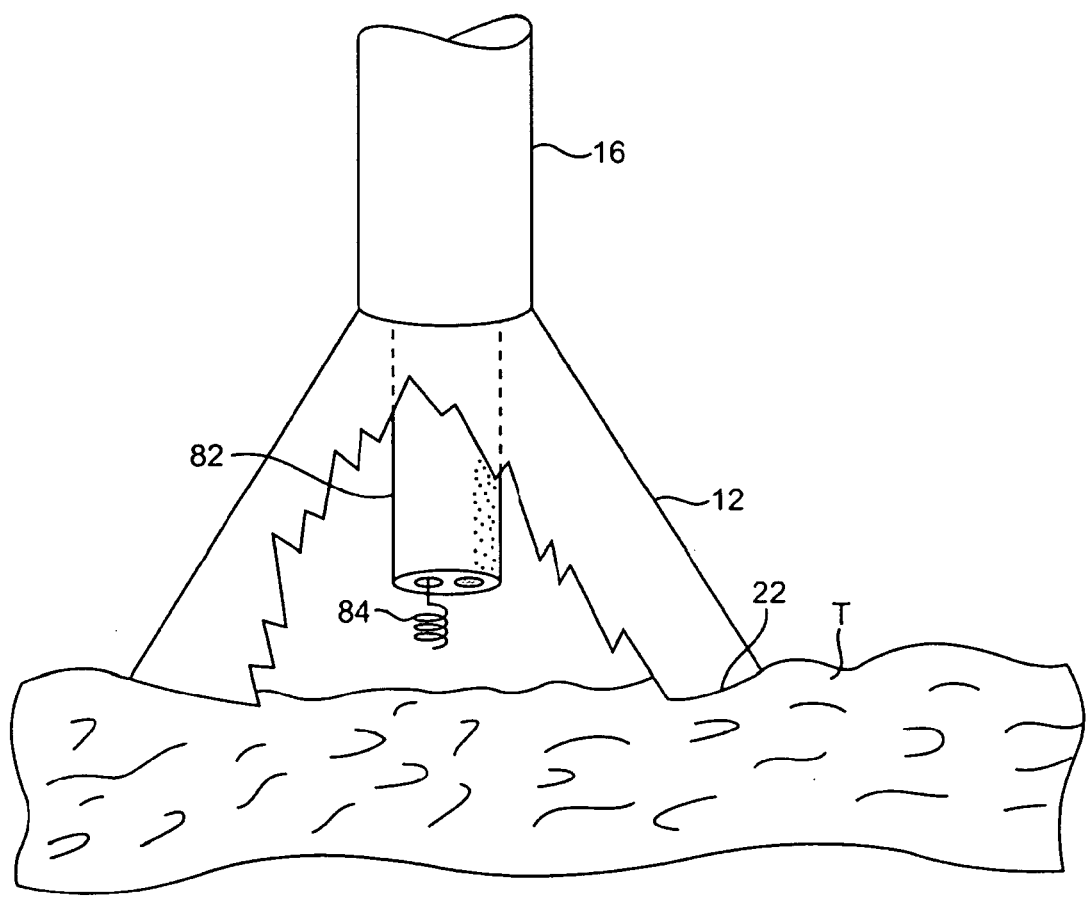
FIGS. 7A and 7B illustrate a variation of an anchoring mechanism such as a helical tissue piercing device for temporarily stabilizing the imaging hood relative to a tissue surface.
Figure 7B:
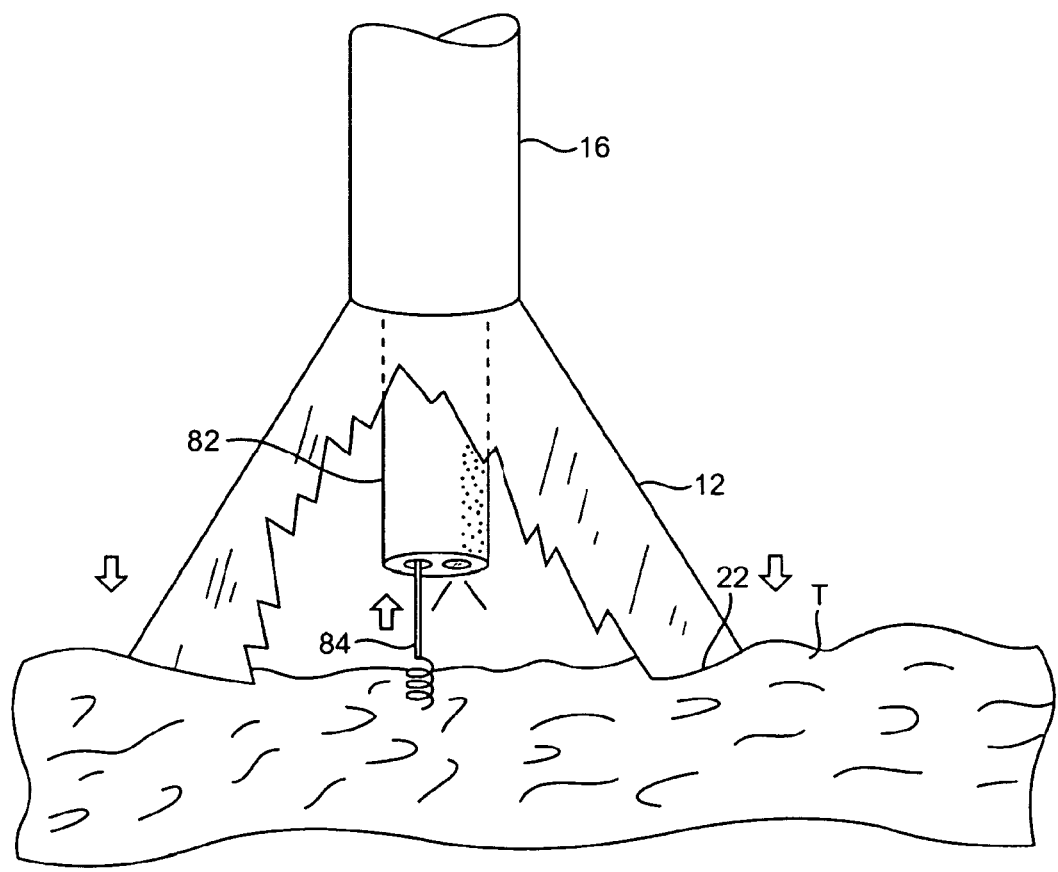

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
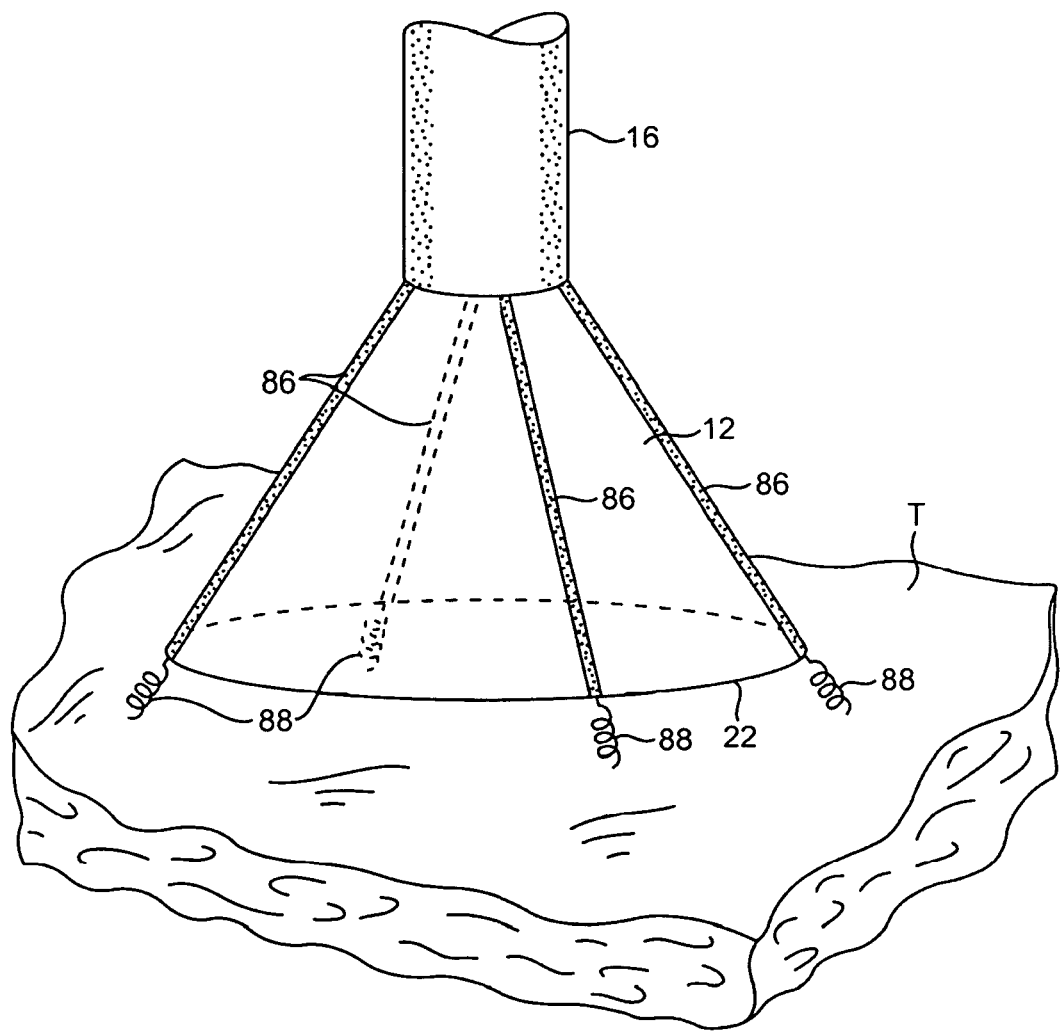
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
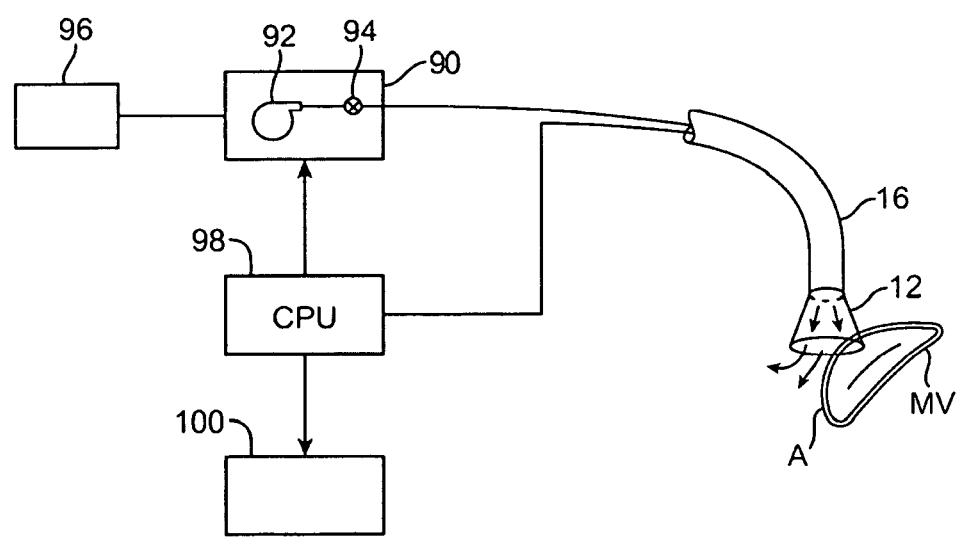
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
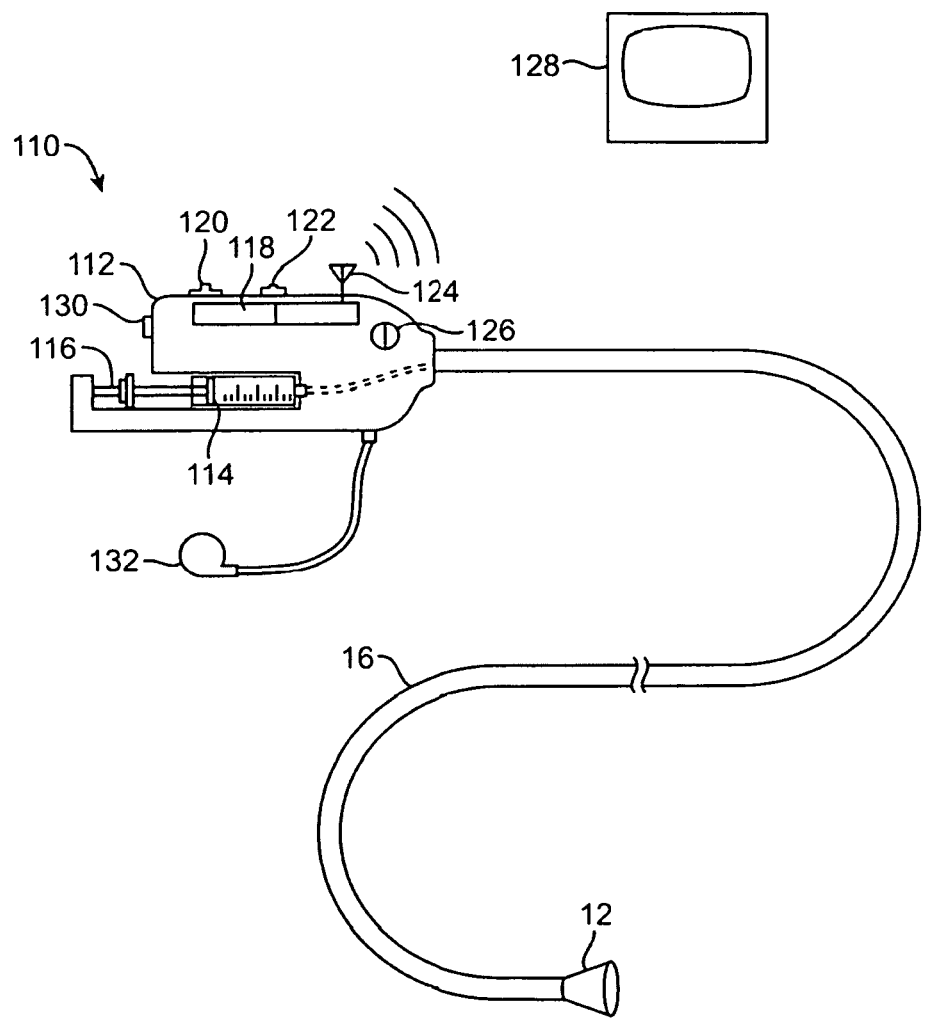
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16.

Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
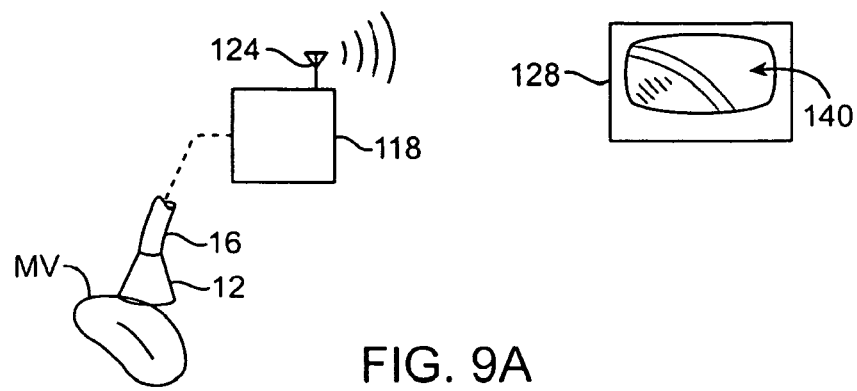
FIGS. 9A to 9C illustrate an example of capturing several images of the tissue at multiple regions.
Figure 9B:
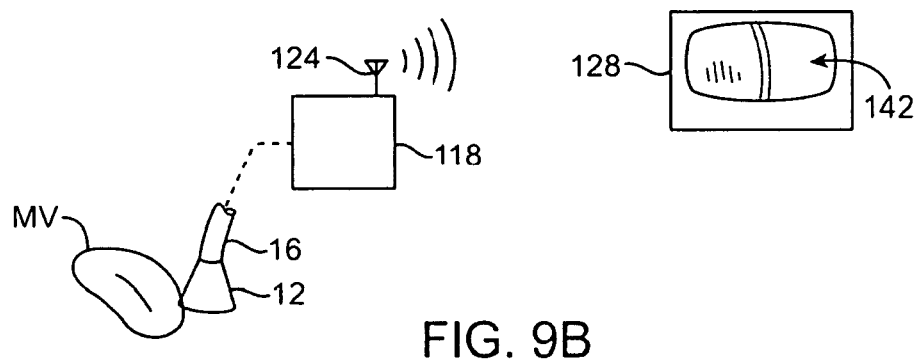
Figure 9C:
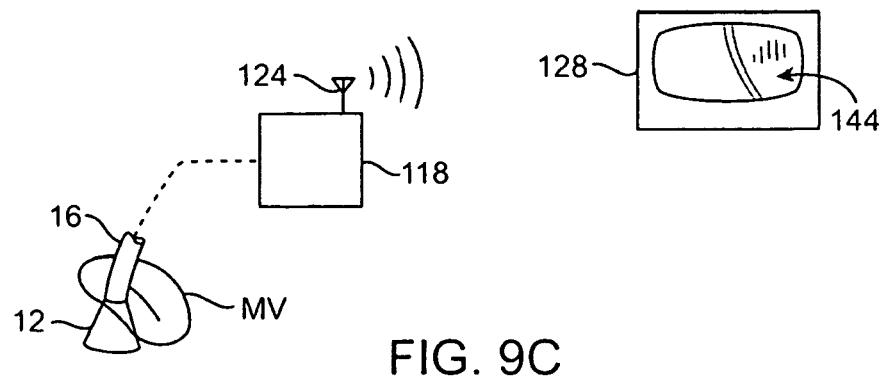

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
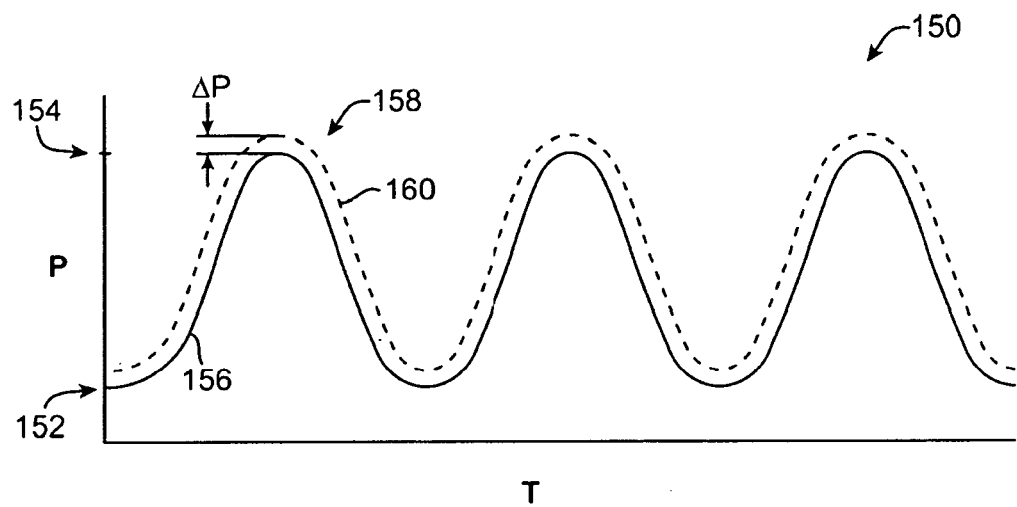
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase $\Delta P$, as illustrated by the pressure difference at the peak systolic pressure 158. This pressure difference, $\Delta P$, may be maintained within imaging hood 12 over the pressure variance of the surrounding blood pressure to maintain a positive imaging fluid pressure within imaging hood 12 to maintain a clear view of the underlying tissue. One benefit of maintaining a constant $\Delta P$ is a constant flow and maintenance of a clear field.

Figure 10B:
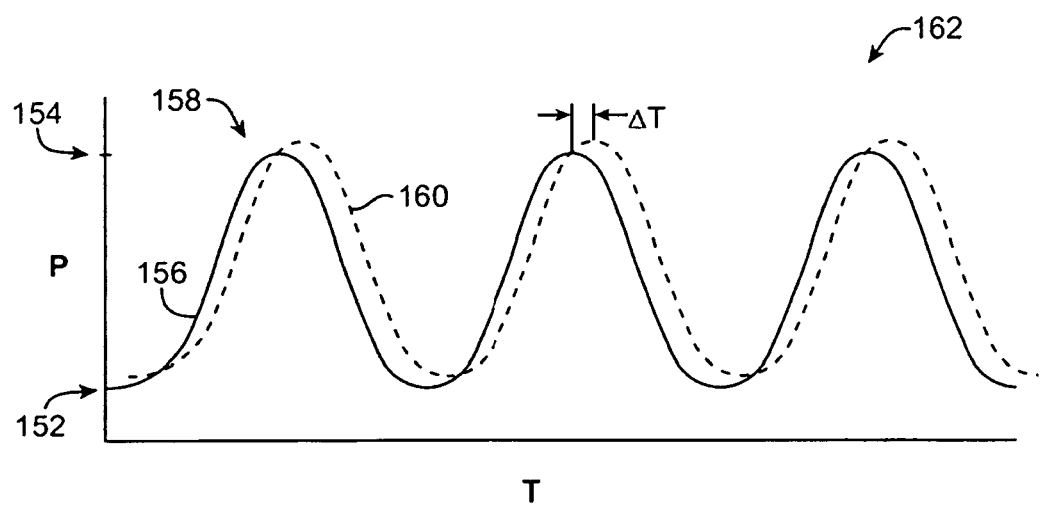

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, $\Delta T$, as illustrated by the shifted fluid pressure 160 relative to the cycling blood pressure 156, although the time delays $\Delta T$ may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

In further controlling the flow of the purging fluid within the hood 12, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood 12 may be maintained for relatively longer periods of time by inhibiting, delaying, or preventing the infusion of surrounding blood into the viewing field.

In utilizing the hood 12 and various instruments through the hood for tissue treatment, hood 12 may be articulated in a variety of configurations to facilitate the access to regions within the heart. For instance, access to the left atrium of a patient's heart for performing treatments such as tissue ablation for atrial fibrillation may require hood 12 to be retroflexed in various configurations to enable sufficient access. Thus, the ability to control the steering or articulation of hood 12 within the patient's heart may facilitate tissue visualization and treatment.

Figure 11A:
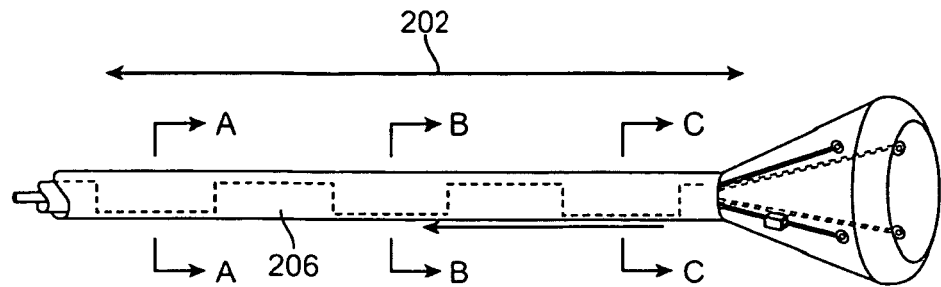
FIGS. 11A and 11B show a side view of a variation of the steerable tissue visualization catheter with multiple plane steering guided by keyhole lumens.
Figure 11B:
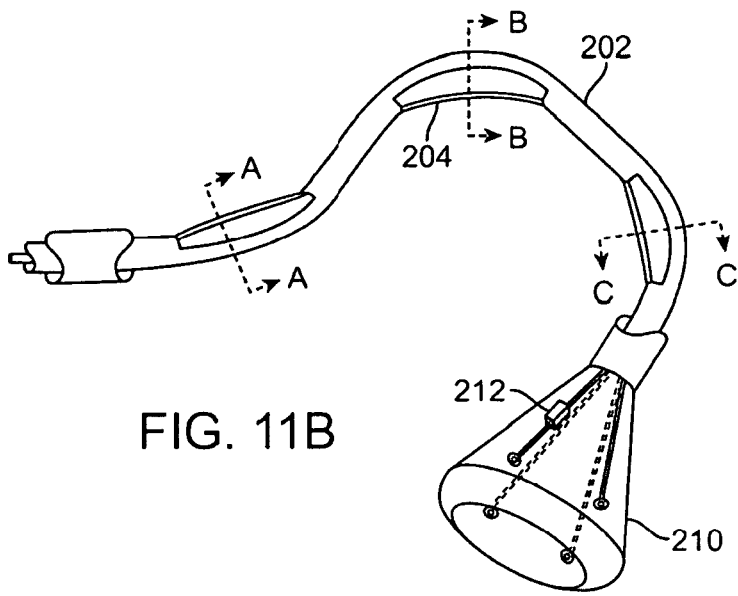
Figure 11C:
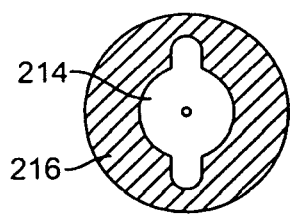
FIGS. 11C to 11E illustrate various keyhole lumen configurations.
Figure 11D:
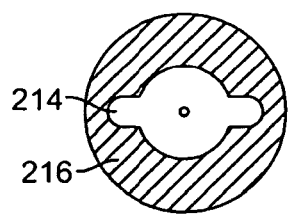
Figure 11E:
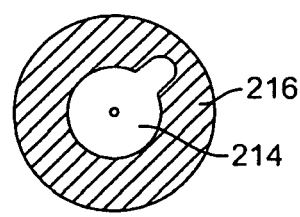

FIG. 11A shows a side view variation of the steerable tissue visualization catheter with multiple plane steering guided by keyhole lumens. As shown in FIG. 11A, one variation of the visualization catheter may comprise a tubular member such as an extrusion 206 having grooves defined off the catheter leaving a pull mechanism exposed at desired intervals. Steerable segment 202 can be laser cut from tubes, double durometer extrusion, and rink links, for example. Pull mechanism 204 is exposed at desired intervals. Distal to extrusion 206 is hood 210 coupled to and extending distally from the steerable segment 202. An imaging element 212 is also found in hood 210 where the imaging element can be a CMOS or CCD camera with light source, as described above. The imaging element 212 can also be a high resolution optical fiber scope (with light source) positioned in one of the channels of the multi-lumen extrusion 206. The steerable segment 202 of the catheter reveals pull wires 204 at desired intervals within extrusion 206. The pull wire 204 can be made from stainless steel, Nitinol, elgiloy, tungsten, etc.

When pull wire 204 is tensioned, the exposed portions of the catheter may function as pivoting sections biasing the catheter to bend in predetermined directions. Keyhole lumens may be utilized through sections of the steerable segment 202, as illustrated in the cross-sectional views of FIGS. 11C, 11D, and 11E which are exemplary cross-sectional views that portions of segment 202 may include. As shown, each respective lumen may define a first main region of the lumen 214 and a second keyed region 216 extending from first main region 214 at predefined orientations. The relative positioning of keyed region 216 relative to main region 214 may be varied to alter the natural direction which segment 202 may articulate or bend. Further details of such a visualization catheter and methods of use are shown and described in U.S. Pat. Pub. 2006/0184048 A1, which is incorporated herein by reference in its entirety.

Figure 12A:
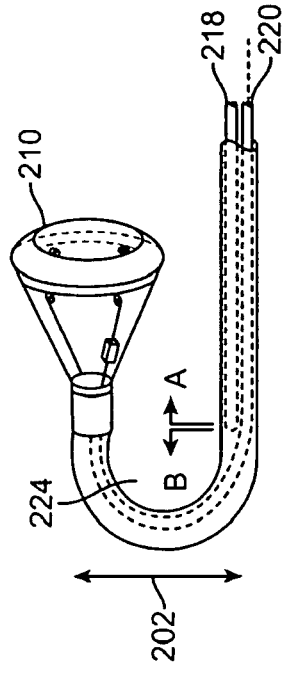
FIGS. 12A to 12D depict side view and end views of the device with a steering guide traveling with the steering catheter.
Figure 12B:
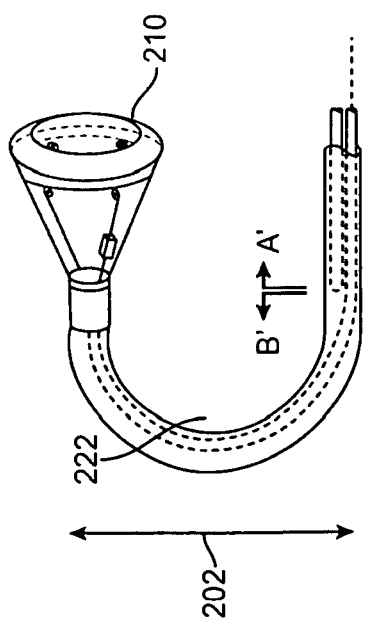
Figure 12D:
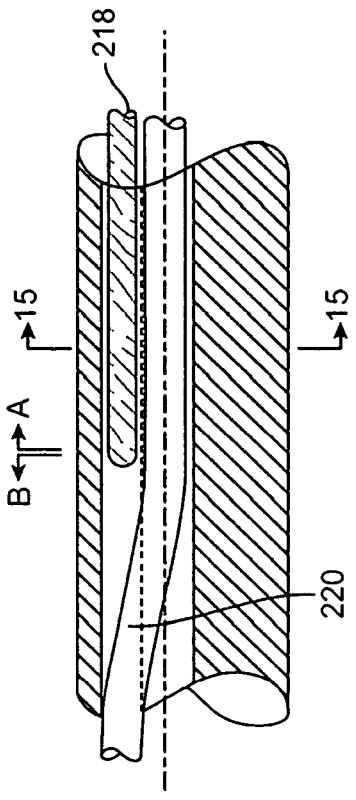
Figure 12C:
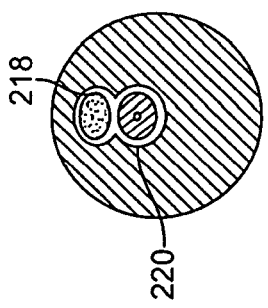

FIGS. 12A and 12B illustrate a comparison of a device having a large bending radius 222 relative to a device having a smaller bending radius 224 in respective steerable segments 202. FIGS. 12A and 12B also both have steering guides 218 and steering actuator 220, the adjustment of which will provide the necessary bend in the catheter shaft. FIG. 12C depicts the cross-sectional view of a steering actuator 220, which can be, e.g. pullwires or a fiberscope. Steering guide 218 directs the bend in the shaft as shown in FIGS. 12A and 12B, and is shown in the cross-sectional end and side views of FIGS. 12C and 12D in relationship to the actuator 220.

Figure 13A:
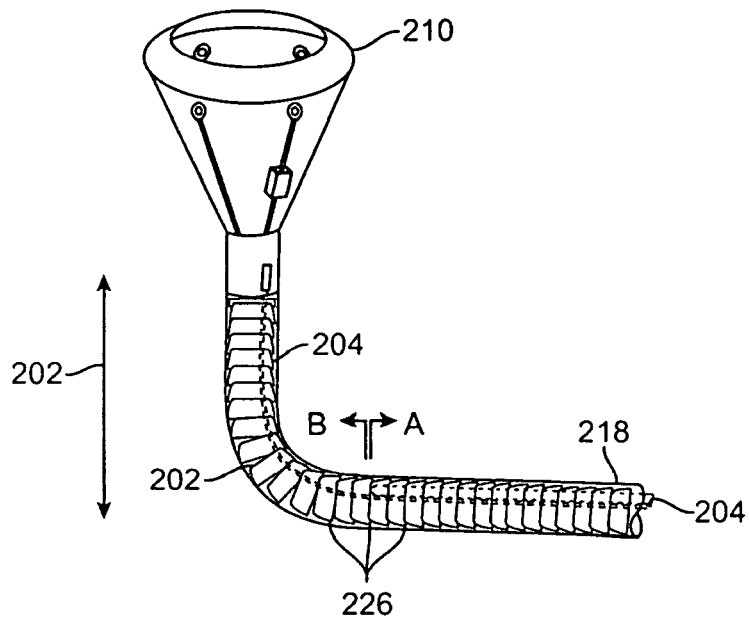
FIGS. 13A to 13C depict side and end views of a variation of a visualization catheter having a pullwire guided by a steering guide.
Figure 13B:
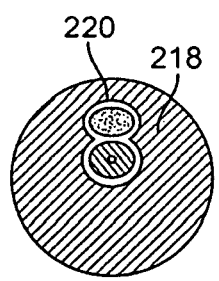
Figure 13C:
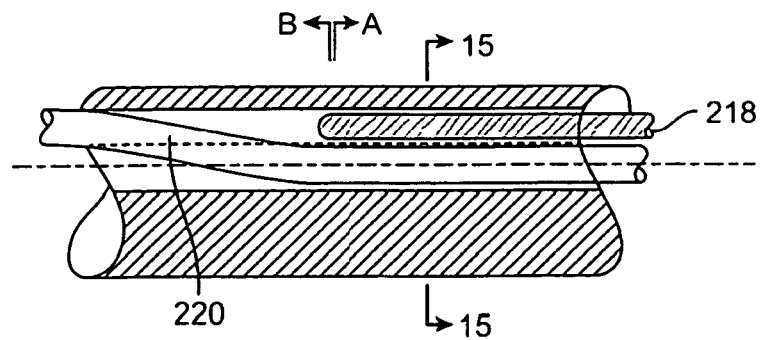

FIG. 13A depicts a device having a pullwire 204 running within a steerable segment 202 having a segmented shaft with articulatable segments 226. Steering guide 218 and actuator 220 are depicted in cross section in FIG. 13B and in side view in FIG. 13C. The steering guide and actuator operate together within the steerable segment 202. The articulatable segments 206 can be bent and conformed along the steerable segment as the guide and actuator slide in relation to each other.

With regard to the articulatable segments 226, various types of links may be utilized to affect a corresponding articulation. The links may be ring links, "bump" links e.g. contoured links having a distal curved surface that is convex in shape, and a proximal curved surface that is concave in shape, such that when serially aligned with a similar link, the curved convex distal surface of one link mates correspondingly with the curved concave proximal surface of the adjacent link and allows the relative pivoting or rocking between the adjacent links along a defined plane. Links may also be pinned links each having a pin running through it, laser cut tubes or double durometer extrusions.

Each of the links 226 may define one or more channels therethrough such that when a plurality of links 226 are aligned and mated to one another, each individual channel forms a continuous lumen through the segment. A lining, such as an elastic heat shrink polymer, may be coated upon the link segments to ensure a smooth surface along the links. Moreover, the links can be made from materials such as stainless steel, PEEK, hard plastics, etc., and manufactured through machining, molding, metal injection molding, etc.

Further examples of links and details of additional variations in steering configurations and mechanisms which may be utilized herein are shown and described in further detail in U.S. patent Application Ser. No. 12/108,812 filed Apr. 24, 2008, which is incorporated herein by reference in its entirety.

Figure 14A:
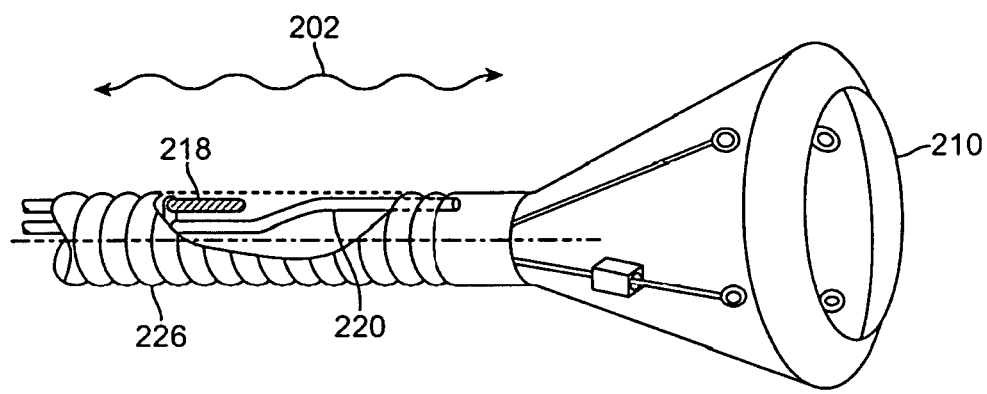
FIGS. 14A and 14B depict pullwires that travel along the steering guide with ring-like steerable links.
Figure 14B:
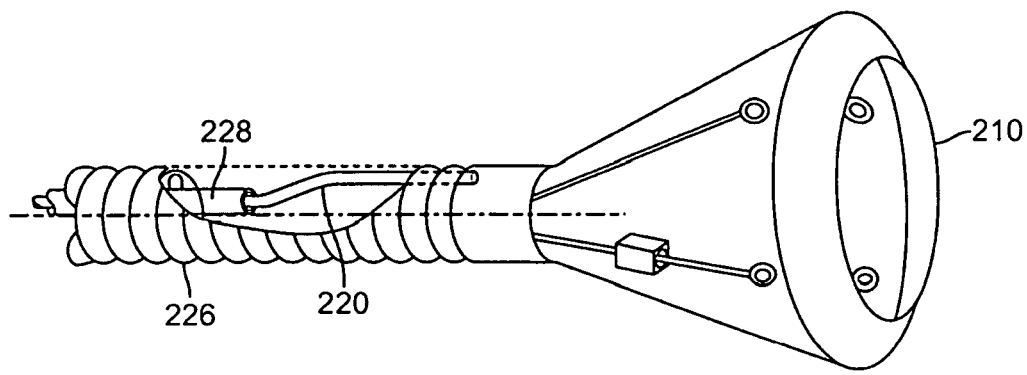

FIG. 14A illustrates a perspective view of a distal section of the device having a hood 210 at a distal end of steerable segment 202. Steering actuator 220 includes in this embodiment pullwires and steering guide tube 218 serves to manipulate the bend achieved by the pullwires 220. The links 226 are shown here as ring links. FIG. 14B depicts a similar variation, except that the steering guide is a tube 228 and as tube 228 retains the steering actuator 220 which in this embodiment is a pullwire. The steerable segment in FIG. 14B also has articulatable segments 226.

Figure 15A:
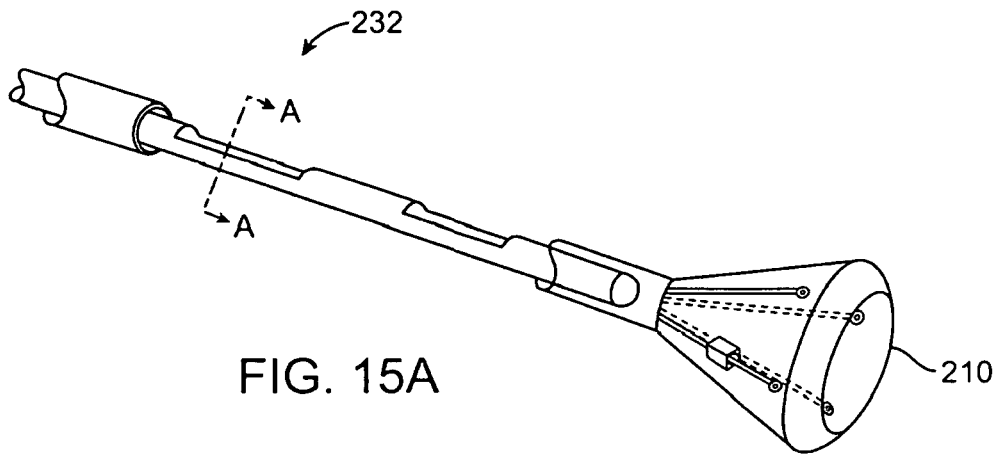
FIGS. 15A to 15D depict proximal and distal segments controllable using catheter extrusions and a pullwire controlled by a keyhole lumen configuration.
Figure 15B:
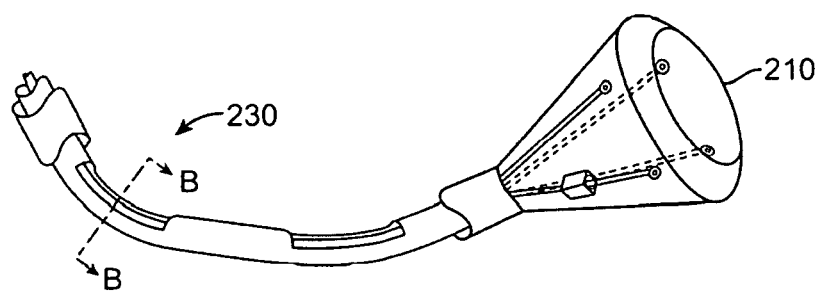
Figure 15C:
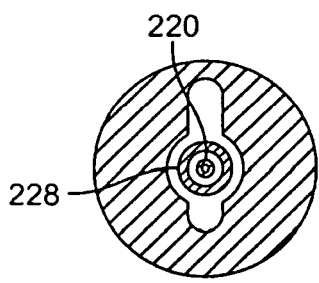
Figure 15D:
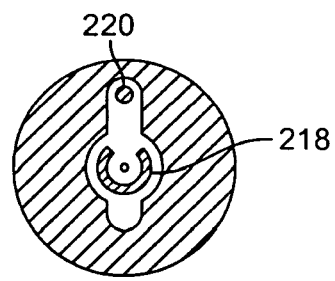

FIGS. 15A and 15B depict a variation having both keyhole extrusion mechanisms and steering guides combined in the same device. The steerable segment 232 may be guided by both keyhole extrusions and steering guides, as described above. The steerable segment 232 can be constructed with various architectures, such as pullwires, pull tubes, imaging fiberscopes, illumination fiberscopes, or tools such as needles, graspers, electrodes, or guidewires for example. In FIG. 15A, steerable segment 232 is shown in a cross-sectional end view in FIG. 15C which depicts both the key-hole extrusions and the steering actuator 220 and guide tube 228. Likewise, FIG. 15D depicts the steerable segment 232 bending 230 where the steering guide and actuator tightly bend using steering guide 218 and steering actuator 220.

Figure 16A:
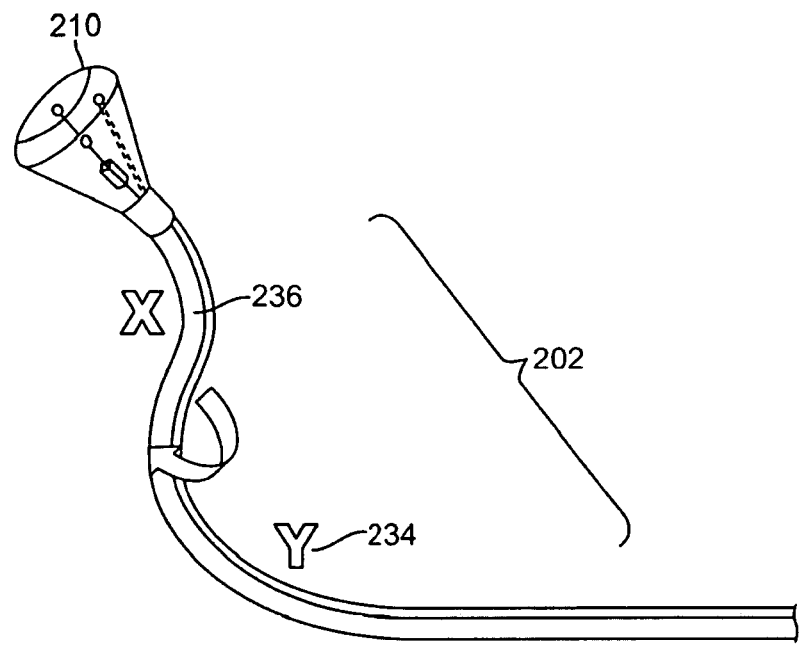
FIGS. 16A to 16G demonstrate the coordinate manipulations of distal and proximal sections to accomplish complex steering maneuvers.

FIGS. 16A to 16G illustrate several types of motion possible with the steerable hood device. In particular, FIG. 16A depicts articulation steering within a plane of the proximal segment 234 (also identified as segment "Y") and "twist" steering or rotational steering of the distal segment 236 (also identified as segment "X") about a longitudinal axis of the catheter, proximal to the hood 210. Twist steering is accomplished using keyhole extrusions depicted above. As a result of the combined motion, steerable segment 202 may bends and twists about its longitudinal axis, as shown.

Figure 16B:
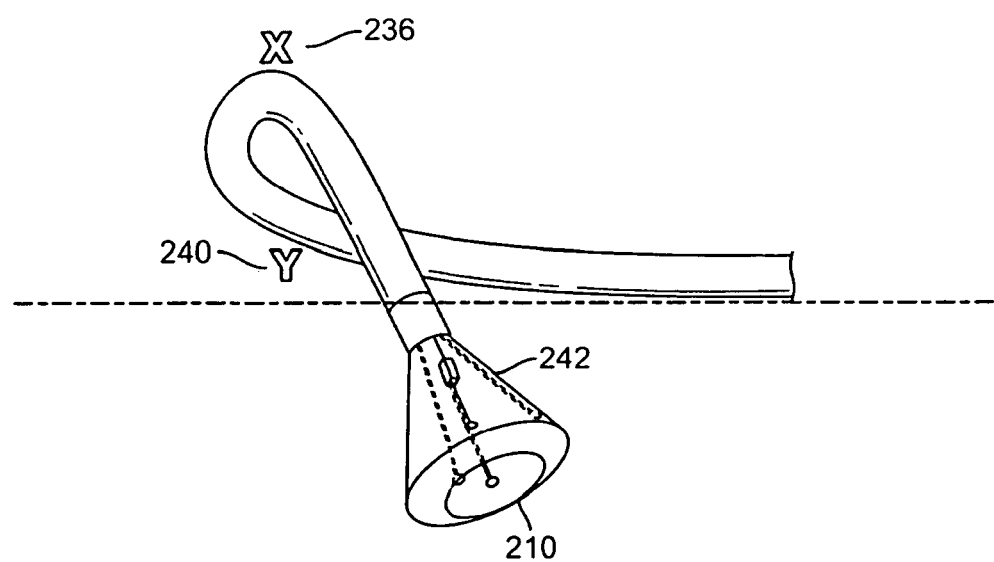
Figure 16C:
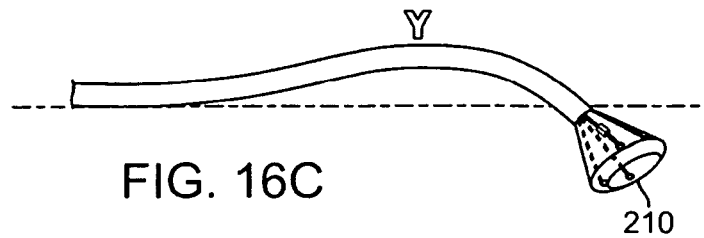
Figure 16D:
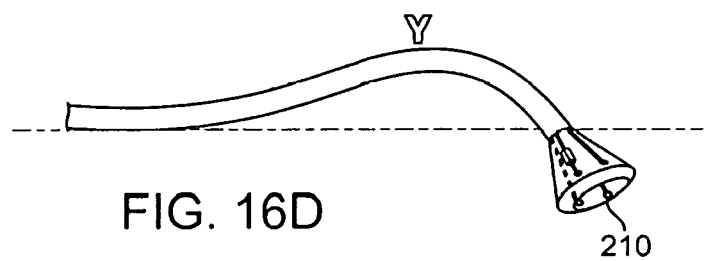
Figure 16E:
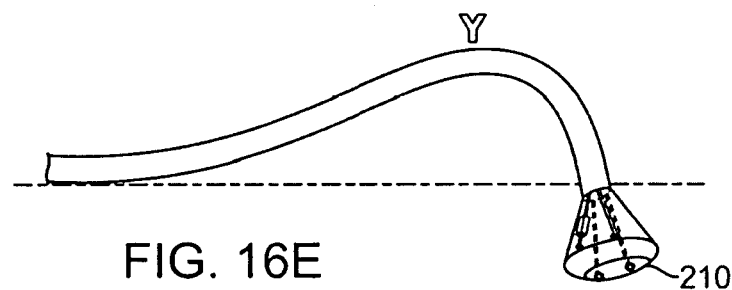

FIG. 16B depicts the device configured with twist steering along distal segment 236 combined with retroflex articulation 242 along proximal segment 240. Retroflex steering can be enabled by steering mechanisms and methods disclosed herein. Retroflex steering allows hood 210 to be configured out-of-plane relative to a proximal portion of the device.

Figure 16F:
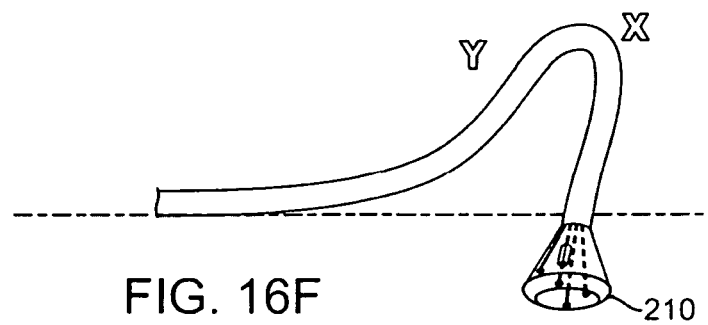
Figure 16G:
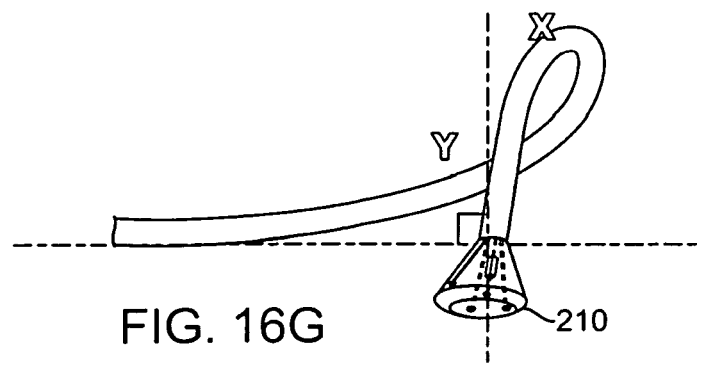

FIGS. 16C to 16G illustrates the hood 210 being configured by a series of complex steering manipulations to allow for engagement of the hood 210 perpendicularly relative to the direction of approach taken to reach the tissue. Accordingly, this series of manipulations could be used to bend the hood 210 directly perpendicular to the direction used to arrive at the target location. In these illustrations, proximal segment Y is shown being articulated to curve within a plane coincident with the catheter in FIGS. 16C to 16E. As proximal segment Y is curved (or once segment Y has been fully articulated), distal segment X may be articulated to twist about itself such that distal segment X is moved out-of-plane with respect to segment Y and the remainder of the catheter, as shown in FIGS. 16F and 16G. This series of manipulations resulting in the perpendicular approach of the hood relative to the rest of the device can be applied to navigate the hood in body lumens, especially when space is limited, for locating and establishing direct visualization of tissue surfaces/features such as the fossa ovalis, the coronary sinus, and pulmonary veins.

Figure 17A:
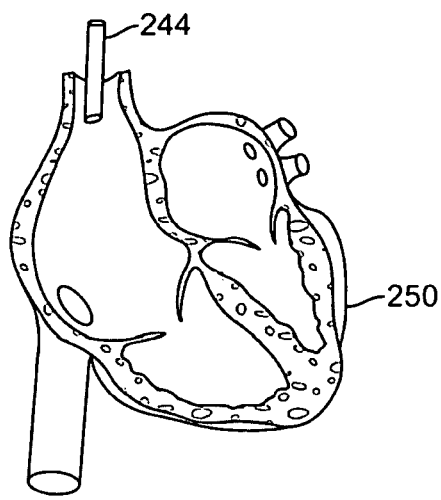
FIGS. 17A to 17D illustrate the device accessing the right atrium of the heart via the superior vena cava to perform complex steering in order to articulate the hood to a target region of interest.
Figure 17B:
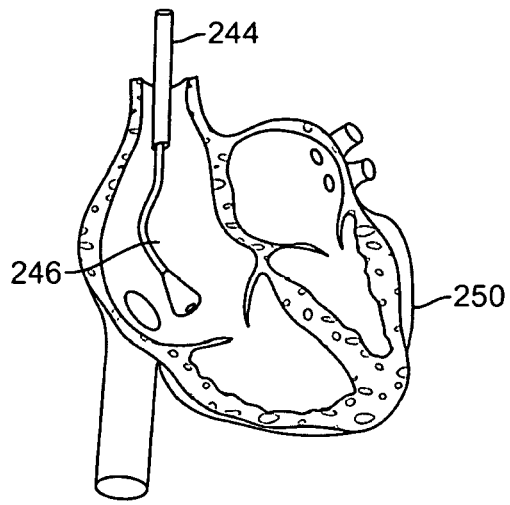
Figure 17C:
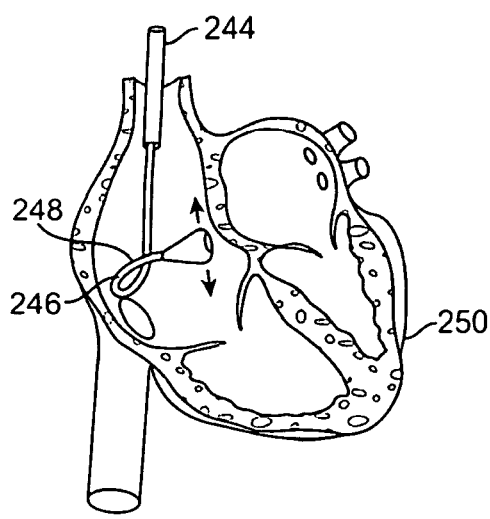
Figure 17D:
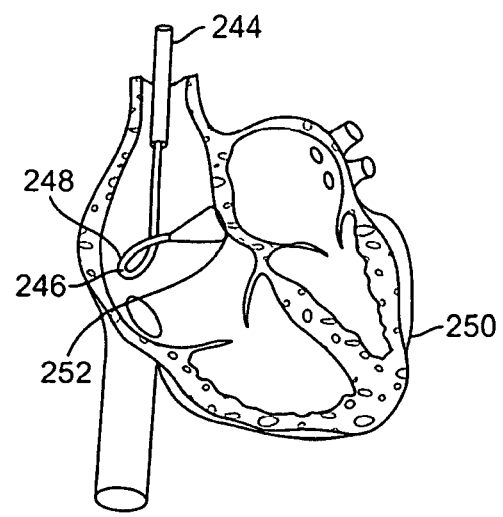

FIGS. 17A to 17D illustrate partial cross-sectional side views of a catheter introduced within the patient's heart 250 and articulated to conform into complex configurations. As shown, an introducer sheath 244 may be advanced intravascularly, in this example through the superior vena cava, into the right atrial chamber to access the atrial septum. Introducer sheath 244 is placed in the right atrium, as in FIG. 17B, and used to deploy the steerable visualization catheter 246 through to the right atrium. At this location, as in FIG. 17C, the catheter 246 may be articulated to form curve 248 in a manner described above such that the hood is moved into an out-of-plane configuration that positions the hood perpendicular to the target tissue surface. FIG. 17D completes the access to the target tissue 252 when the distal hood contacts the tissue surface in a perpendicular angle, facilitated by the complex curve steering.

Figure 18A:
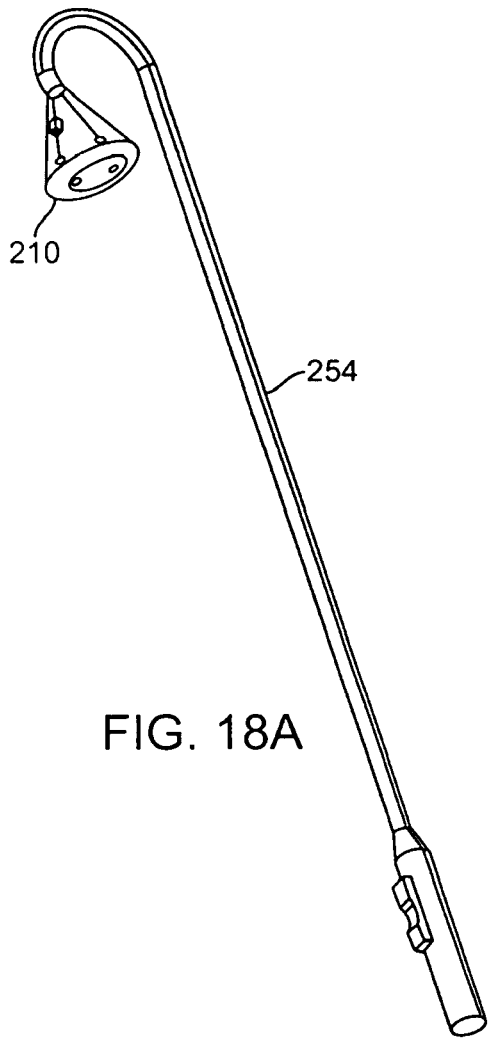
FIGS. 18A to 18C depict a catheter having a steerable retro-flexing introducer sheath.
Figure 18B:
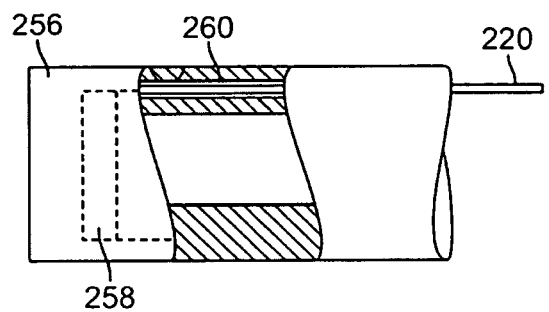
Figure 18C:
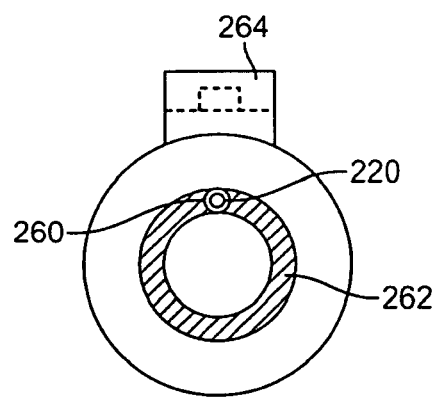

FIGS. 18A to 18C depict perspective, side, and end views of a variation of the tissue visualization catheter having a steerable retro-flexing sheath 254 that controls the proximal segment, as shown in FIG. 18A. FIG. 18B depicts a partial cross-sectional side view a lumen defined in the wall of the sheath 260 to house a pullwire 220 or other steering mechanism. The pullwire 220 is terminated at distal end 258 of the introducer sheath 254 while the introducer sheath distal end 256 may extend beyond the termination region of the pullwire 220. FIG. 18C depicts further details of the introducer sheath 262 in a cross-sectional end view illustrating pullwire 220 housed in lumen 260 within the wall of the sheath. Proximal handle 264 controls the pullwire or other steering mechanism.

Figure 19A:
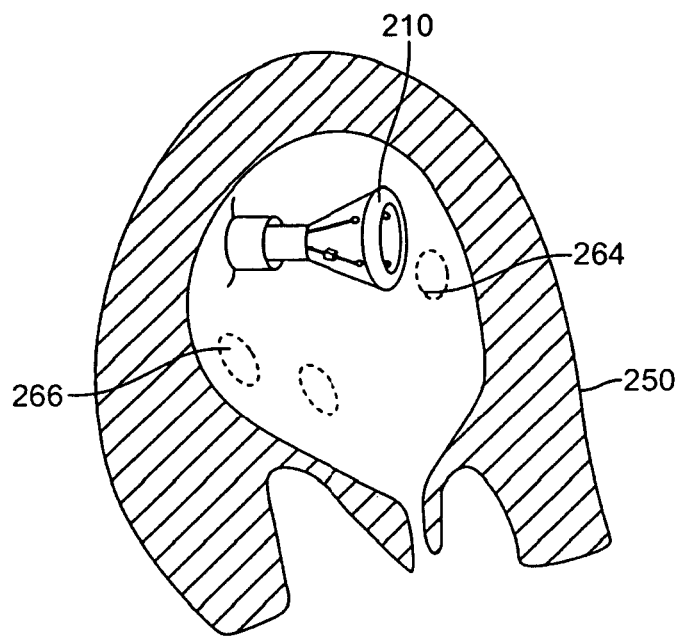
FIGS. 19A and 19B depict the device accessing the left atrium of the heart through the septum.
Figure 19B:
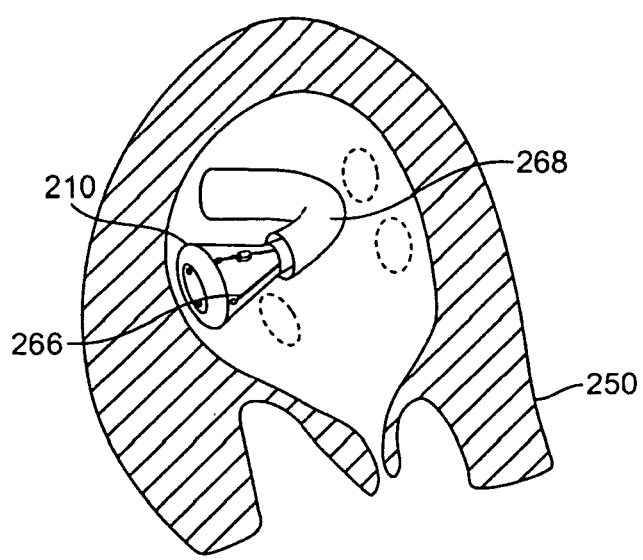

FIGS. 19A and 19B depict a steerable introducer sheath directing a visualization hood 210 into the heart 250 to access the left 264 and right 266 pulmonary veins. Curve 268 is generated by the manipulations of the introducer sheath controlling the directionality of the hood 210 in FIG. 19B.

FIGS. 20A to 20C show perspective views of an apparatus having a push steering mechanism. FIG. 20A shows steerable segment 202 supported by at least one rigid lateral support arm 272 attached to a push steering collar 274 on the proximal end and to a hinge 270 at the base of the visualization hood 210. FIG. 20B depicts the curvature possible in steerable segment 202 when segment 202 is pushed from a proximal end to pivot hood 210 about hinge 270. In FIG. 20B, the push steering mechanism is abutted at its proximal end with a flexible sheath 276 to facilitate intravascular advancement. Push steering collar 274 and rigid lateral support arms 272 push at the base of the hood 210 through the hinge connection that manipulates the hood 210. FIG. 20C demonstrates an ability of the push steering mechanism to torque the catheter along a longitudinal axis to steer the hood to multiple planes. Flexible sheath 276 and support arms 272 direct and rotate distal steering segment 202.

Figure 21A:
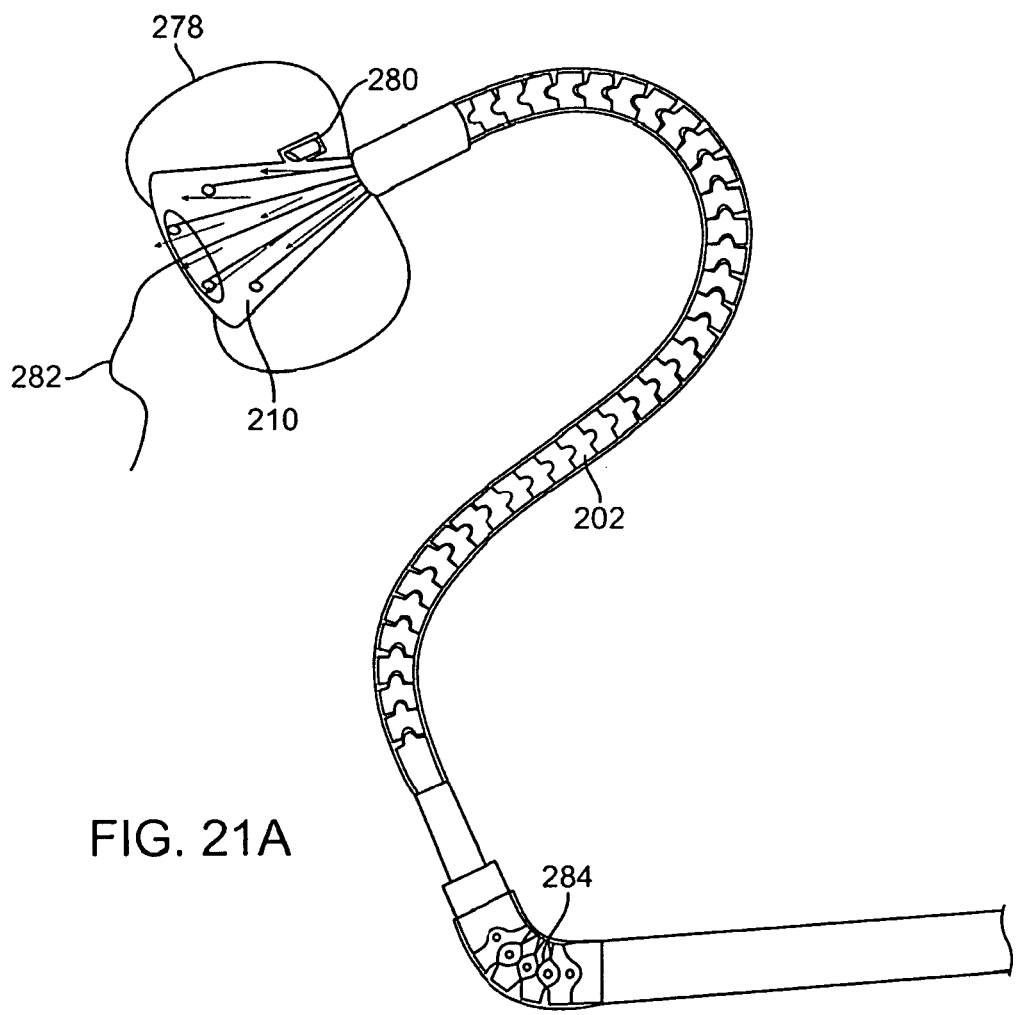
FIGS. 21A to 21C depict variations of the expandable visualization hood.
Figure 21B:
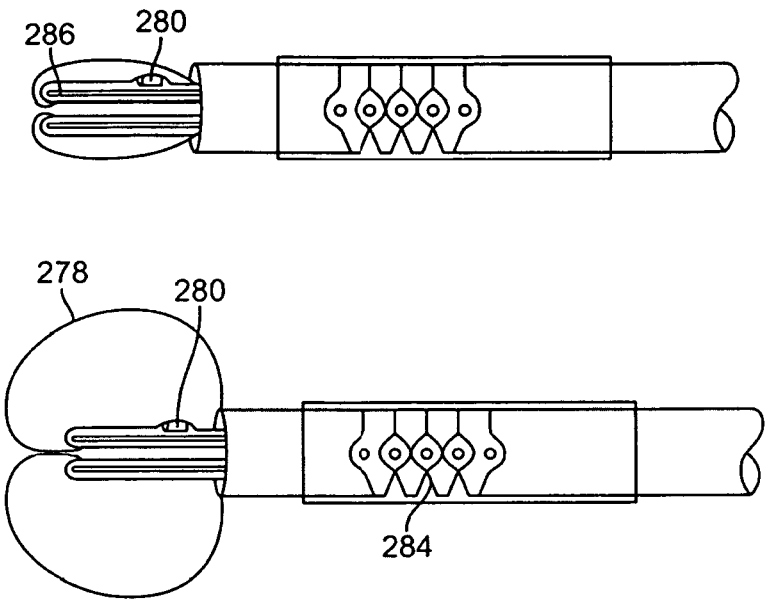
Figure 21C:
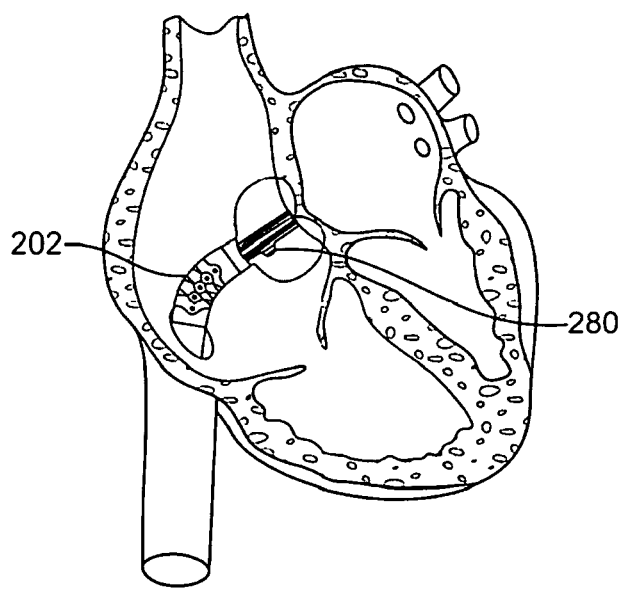

FIGS. 21A to 21C depict another variation of an expandable visualization hood 278 in which an imaging element such as CMOS/CCD can be mounted. A guidewire 282 can be used to access the hood to the region of interest. As shown in FIG. 21A, a steerable double bend segment 202 can have articulating links such as the concave/convex links described previously. More proximal still, the steerable sheath 284 is constructed of steerable links, in the case as depicted here, pin links in which pins connect separate articulating links to one another in a sequence. FIG. 21B illustrates detail side views of the pre-deployed visualization hood 286, configured here as an expandable membrane, having imaging element 280 positioned within. The expandable visualization membrane 278 may be fully deployed once it is deployed from the catheter sheath. FIG. 21C shows an expandable visualization hood 278 and imaging element 280 articulating in the heart in order to accomplish visualization of a region of tissue in a heart chamber.

Figure 22B:
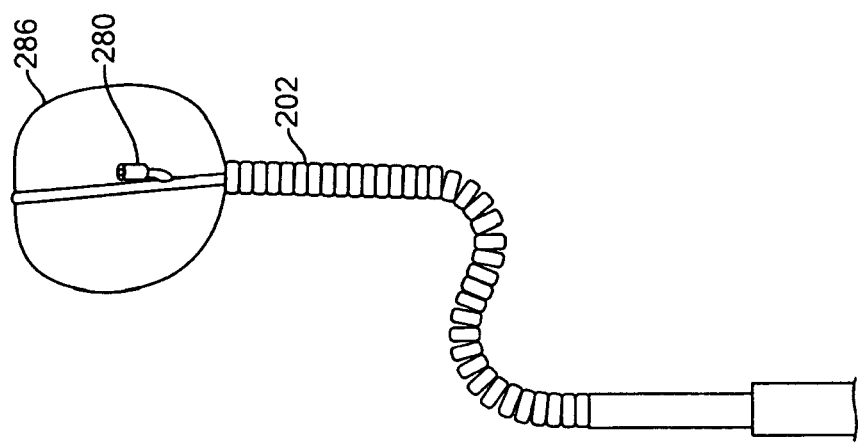
FIGS. 22A and 22B depict an alternative steering mechanism with an expandable visualization hood.
Figure 22A:
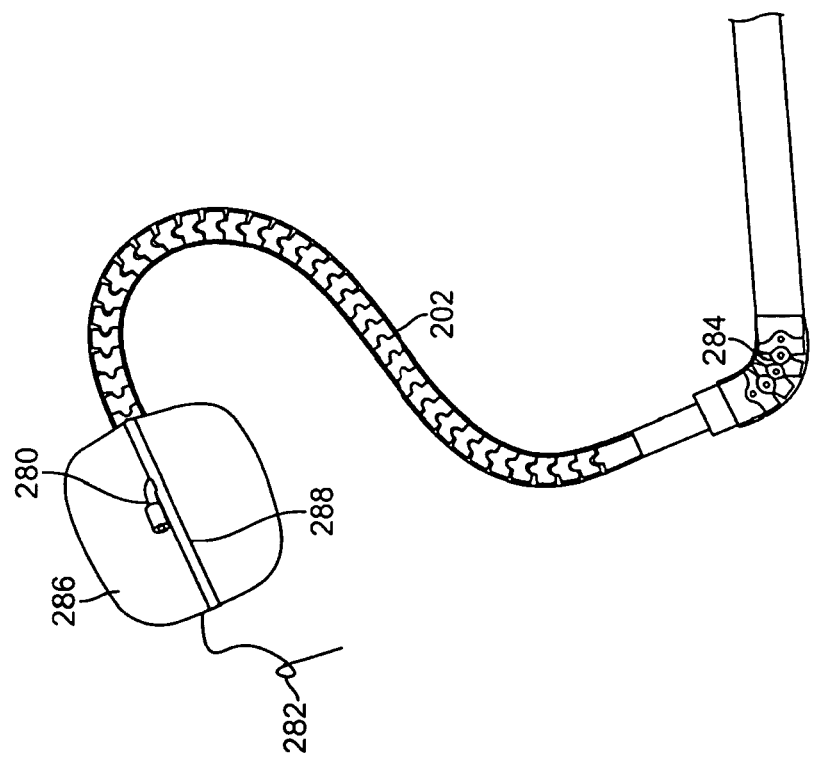

FIG. 22A depicts another variation of an expandable visualization membrane 286 through which is defined a working channel 288 and imaging element 280 positioned therealong within membrane 286. Guidewire 282 extends through the working channel 288 in order to position the apparatus accurately at the target region. As previously described, steerable segment 202 may be formed from, e.g., bump links, and the steerable sheath proximal to segment 202 comprising, e.g., pin links. FIG. 22B depicts an expandable visualization membrane 286 having a working channel, where the steerable segment 202 is composed of ring links to provide high force transmission and steerability to the visualization hood as it is guided and positioned to a site.

Figure 24:
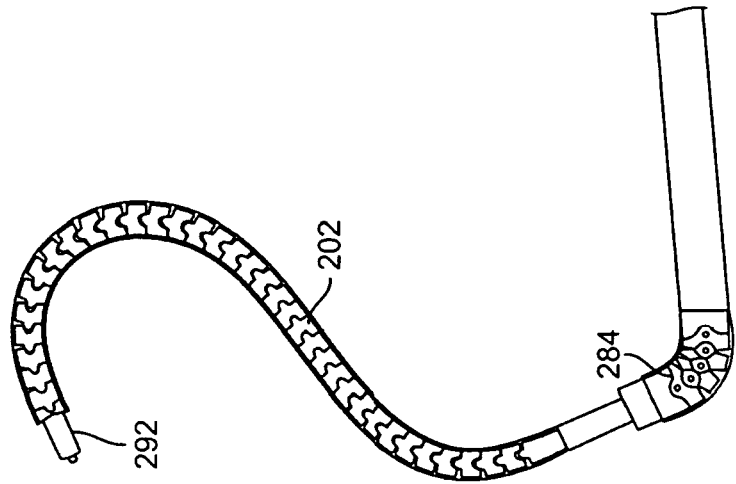
FIG. 24 depicts a complex steering mechanism to manipulate an infrared endoscope at the distal end.
Figure 23:
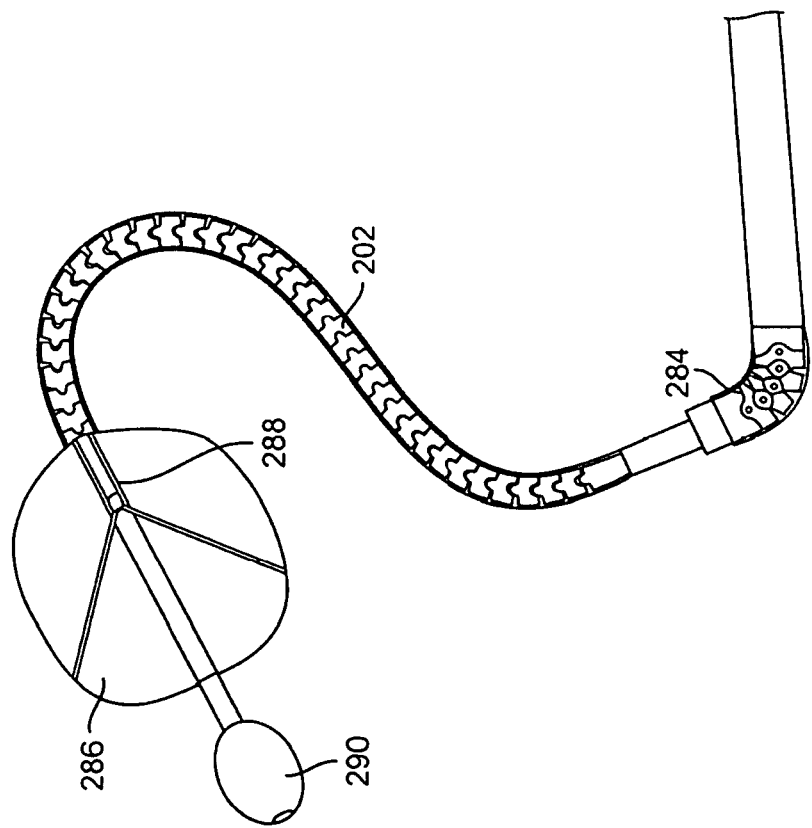
FIG. 23 depicts an expandable visualization hood, having a distal anchoring member and an ablation optical source.

FIG. 23 depicts a side view of another variation of the apparatus having an expandable visualization membrane 286 and a distal expandable anchoring member 290. The visualization membrane 286 contains an energy transmitter such as laser optics 288 for ablation therapy under direct visualization. As before, the steerable segment 202 depicts links that control the movement of that section. FIG. 24 depicts the apparatus having an infrared camera and light source 292 at the distal end and a steerable segment 202 as described above.

Figure 25A:
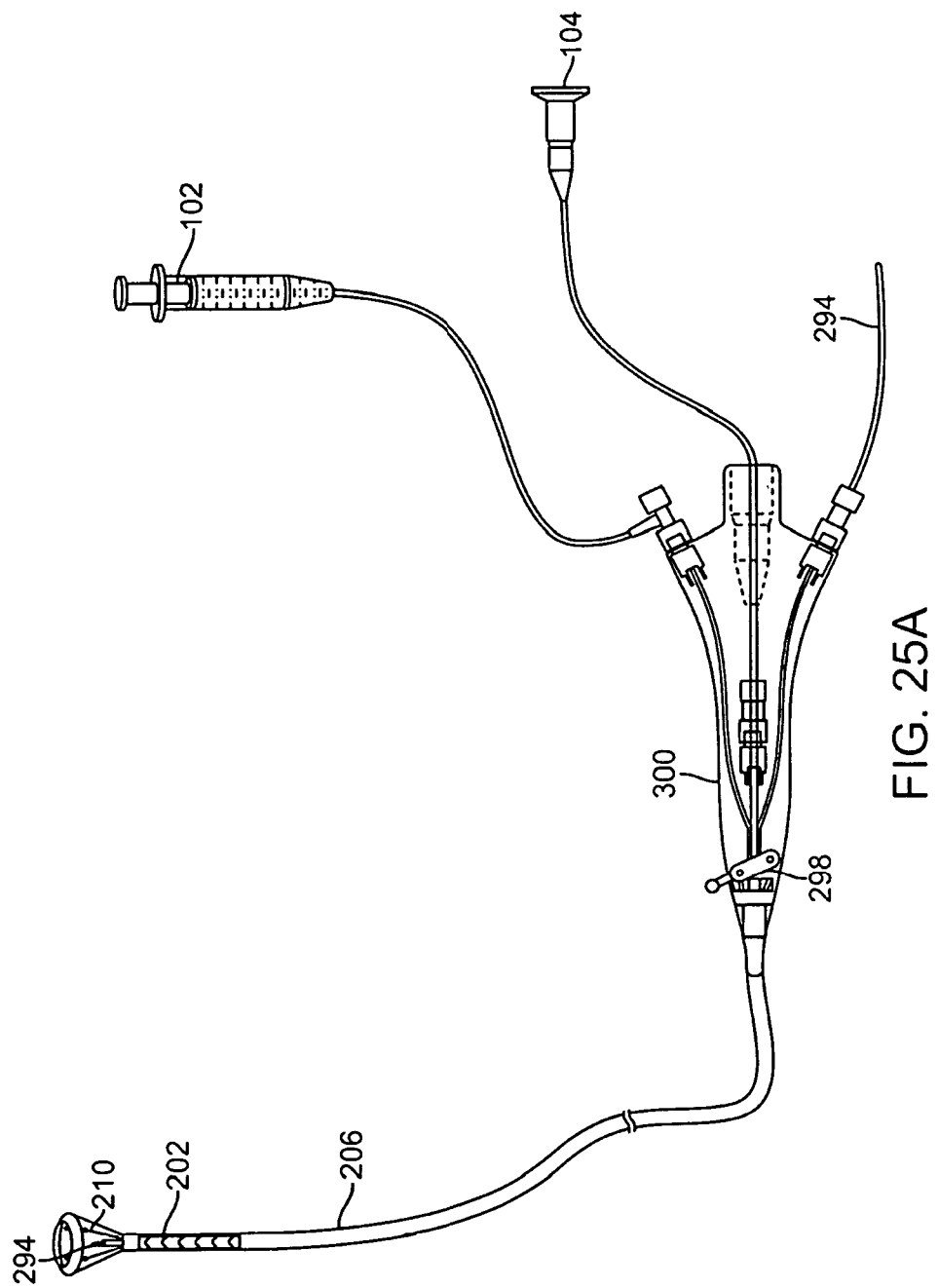
FIGS. 25A to 25D depict an apparatus having a handle at the proximal end for facilitating control of multiple functions in the apparatus and for supporting various tools.
Figure 25B:
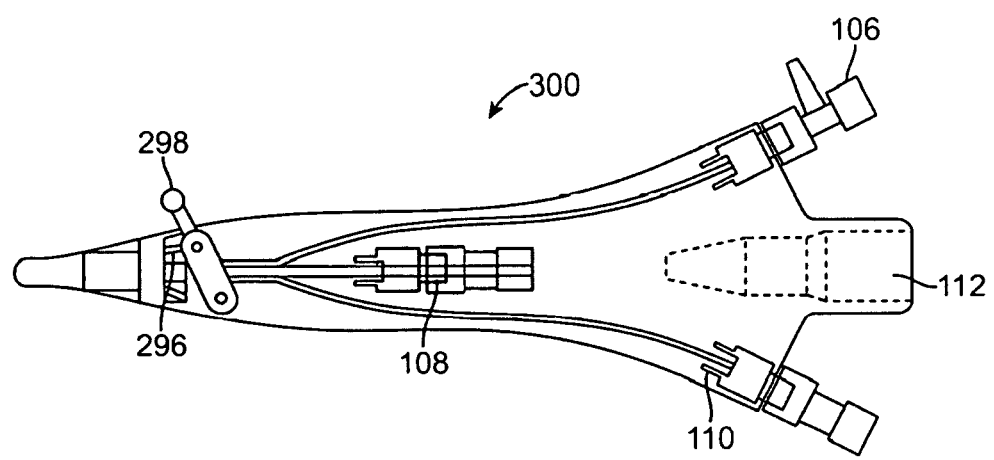
Figure 25D:
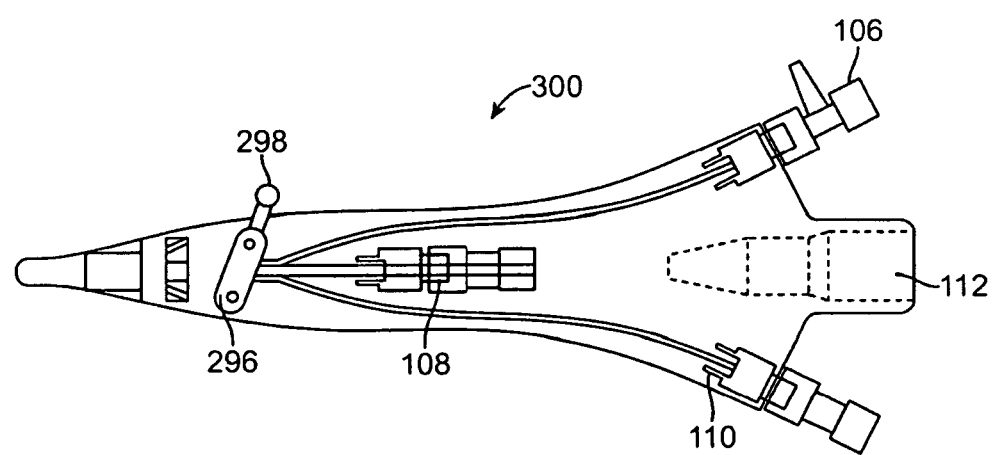
Figure 25C:
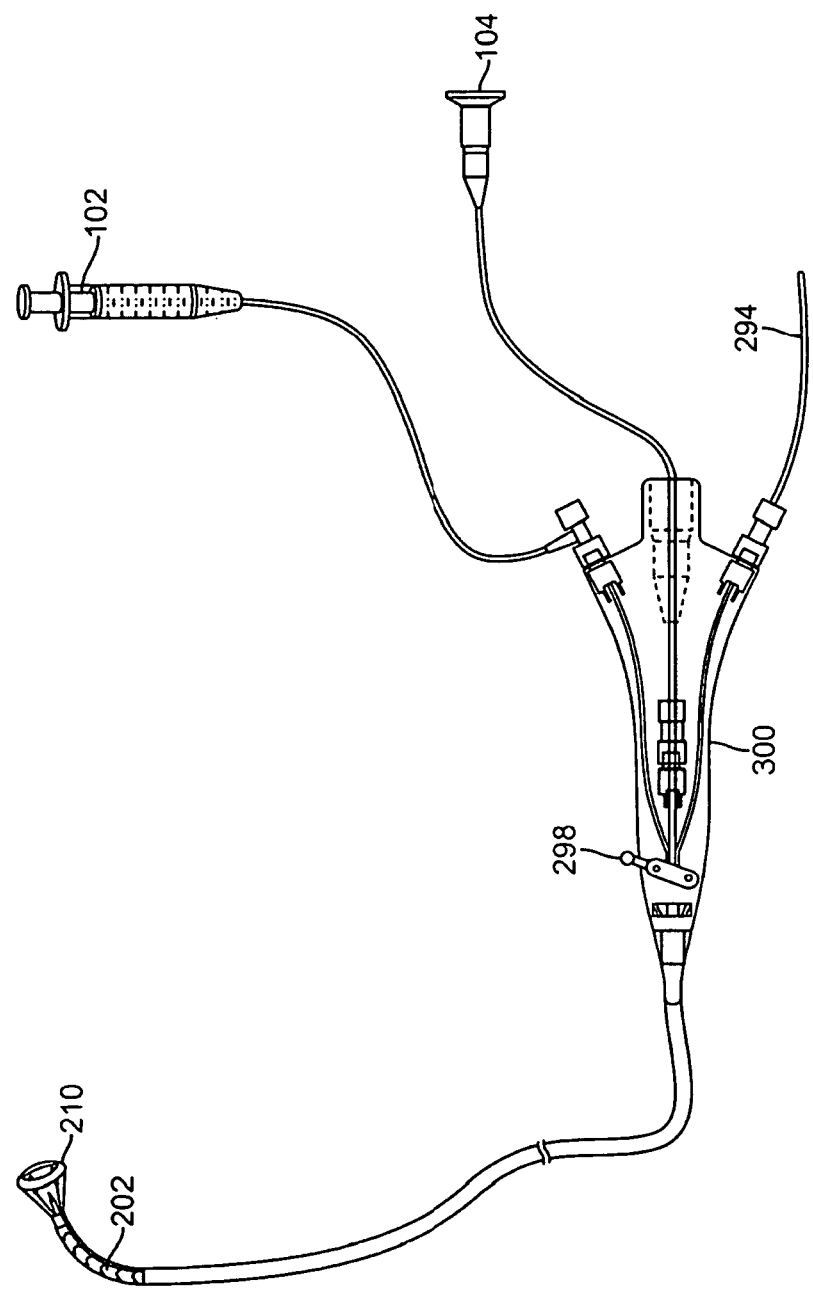

FIG. 25A depicts an assembly view of a system having multiple tools introduced through handle 300. Tools depicted here include a syringe for purging the hood 102, a fiberscope 104, and a needle with a sheath 294. Also depicted are a steering lever 298 connected to pullwire 296. The steerable segment 202 of the apparatus may include, e.g., bump links, a multi-lumen extrusion 206, and a needle in sheath 294. FIG. 25B depicts a closer view of the control handle 300 having steering lever 298 at which pullwire 296 terminates. Valves for passing tools such as a fiberscope 108, a valve for passing tools such as a needle 110, and housing for the proximal end imaging elements such as a camera connector of a fiber scope 112 are also shown. FIG. 25C shows a larger view of steering lever 298 in its interaction with steerable segment 202 to manipulate hood 210. Lever 298 in the rear position provides tension to the pull wires threaded along the steerable segment 202. Various tools are also depicted. FIG. 25D depicts handle 300 having steering lever 298 in a rear position providing tension to pull wires 296 as the steering lever pivots about a pin hinge in order to provide tension on the pullwires.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An apparatus for accessing a difficult-to-reach tissue surface in a region of a body having a continuous interfering blood flow comprising:
   a flexible deployment catheter shaft capable of intravascular advancement having an articulatable assembly near or at a distal portion of the catheter, the articulatable assembly having a proximal steerable section and a distal steerable section connected distally of the proximal section;
   a barrier or membrane attached to a distal end of the distal steerable section such that the barrier or membrane forms a non-inflatable fluid impermeable barrier which is self-expanding from a delivery profile to a deployment profile which defines an open area surrounded by the barrier or membrane, wherein the open area is in fluid communication with a lumen defined through the catheter and with an environment external to the barrier or membrane; and, a visualization element disposed within or adjacent to the open area of the barrier or membrane for visualizing tissue adjacent to the open area, the proximal steerable section articulates with a steering guide traveling along a steering actuator, and the distal steerable section is adapted to articulate within one or more planes relative to a longitudinal axis of the proximal steerable section.

2. The apparatus of claim 1, further comprising pullwires traveling along the steering guide.

3. The apparatus of claim 1, further comprising a ring-linked steerable segment.

4. The apparatus of claim 1, having a pullwire guided by the steering guide.

5. The apparatus of claim 1, having a pullwire threaded along a steering tube within a ring-linked proximal steerable section.

6. The apparatus of claim 1, further comprising an ablation element positionable at the distal end of the catheter shaft.

* * * * *